US009101690B2

(12) United States Patent
Deisseroth et al.

(10) Patent No.: US 9,101,690 B2
(45) Date of Patent: Aug. 11, 2015

(54) LIGHT-ACTIVATED CATION CHANNEL AND USES THEREOF

(75) Inventors: Karl Deisseroth, Palo Alto, CA (US); Edward S. Boyden, Cambridge, MA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 205 days.

(21) Appl. No.: 13/555,981

(22) Filed: Jul. 23, 2012

(65) Prior Publication Data

US 2013/0184817 A1    Jul. 18, 2013

Related U.S. Application Data

(62) Division of application No. 11/459,636, filed on Jul. 24, 2006, now Pat. No. 8,906,360.

(60) Provisional application No. 60/701,799, filed on Jul. 22, 2005.

(51) Int. Cl.
| | |
|---|---|
| *A61F 2/18* | (2006.01) |
| *A61L 27/28* | (2006.01) |
| *A61L 27/36* | (2006.01) |
| *A61K 31/137* | (2006.01) |
| *A61K 31/353* | (2006.01) |
| *A61K 31/405* | (2006.01) |
| *A61K 31/4172* | (2006.01) |
| *A61N 5/06* | (2006.01) |
| *C07K 14/705* | (2006.01) |
| *G01N 33/68* | (2006.01) |
| *A61K 35/30* | (2015.01) |
| *A61K 38/00* | (2006.01) |
| *A61K 48/00* | (2006.01) |

(52) U.S. Cl.
CPC ............... *A61L 27/3604* (2013.01); *A61F 2/18* (2013.01); *A61K 31/137* (2013.01); *A61K 31/353* (2013.01); *A61K 31/405* (2013.01); *A61K 31/4172* (2013.01); *A61K 35/30* (2013.01); *A61N 5/0622* (2013.01); *C07K 14/705* (2013.01); *G01N 33/6872* (2013.01); *A01K 2217/05* (2013.01); *A01K 2227/105* (2013.01); *A01K 2227/40* (2013.01); *A01K 2227/703* (2013.01); *A01K 2227/706* (2013.01); *A61K 38/00* (2013.01); *A61K 48/00* (2013.01); *C07K 2319/60* (2013.01); *C12N 2740/15043* (2013.01); *C12N 2740/15071* (2013.01); *G01N 2500/04* (2013.01); *Y10S 530/82* (2013.01)

(58) Field of Classification Search
None
See application file for complete search history.

(56) References Cited

U.S. PATENT DOCUMENTS

| | | | |
|---|---|---|---|
| 2,968,302 | A | 1/1961 | Fry et al. |
| 3,131,690 | A | 5/1964 | Innis et al. |
| 3,499,437 | A | 3/1970 | Balamuth et al. |
| 3,567,847 | A | 3/1971 | Price |
| 4,343,301 | A | 8/1982 | Indech |
| 4,559,951 | A | 12/1985 | Dahl et al. |
| 4,616,231 | A | 10/1986 | Autrey et al. |
| 4,865,042 | A | 9/1989 | Umemura et al. |
| 4,879,284 | A | 11/1989 | Land et al. |
| 5,032,123 | A | 7/1991 | Katz et al. |
| 5,041,224 | A | 8/1991 | Ohyama et al. |
| 5,082,670 | A | 1/1992 | Gage et al. |
| 5,249,575 | A | 10/1993 | Di Mino et al. |
| 5,267,152 | A | 11/1993 | Yang et al. |
| 5,290,280 | A | 3/1994 | Daikuzono et al. |
| 5,330,515 | A | 7/1994 | Rutecki et al. |
| 5,445,608 | A | 8/1995 | Chen et al. |
| 5,460,950 | A | 10/1995 | Barr et al. |
| 5,460,954 | A | 10/1995 | Lee et al. |
| 5,470,307 | A | 11/1995 | Lindall |
| 5,495,541 | A | 2/1996 | Murray et al. |
| 5,520,188 | A | 5/1996 | Hennige et al. |
| 5,527,695 | A | 6/1996 | Hodges et al. |
| 5,550,316 | A | 8/1996 | Mintz |
| 5,641,650 | A | 6/1997 | Turner et al. |
| 5,703,985 | A | 12/1997 | Owyang et al. |

(Continued)

FOREIGN PATENT DOCUMENTS

| | | |
|---|---|---|
| EP | 1 334 748 | 8/2003 |
| EP | 1873566 | 1/2008 |
| JP | 2006-295350 | 10/1994 |
| WO | WO 00/27293 | 5/2000 |
| WO | WO 01-25466 | 4/2001 |
| WO | WO 03/106486 A2 | 2/2003 |

(Continued)

OTHER PUBLICATIONS

Nagel et al. "Channelrhodopsin-2, a directly light-gated cation-selective membrane channel." Proceedings of the National Academy of Science USA (2003); 100: pp. 13940-13945.*

(Continued)

*Primary Examiner* — Thaian N Ton
*Assistant Examiner* — Titilayo Moloye
(74) *Attorney, Agent, or Firm* — Bozicevic, Field & Francis LLP; Paula A. Borden

(57) ABSTRACT

The present invention provides compositions and methods for light-activated cation channel proteins and their uses within cell membranes and subcellular regions. The invention provides for proteins, nucleic acids, vectors and methods for genetically targeted expression of light-activated cation channels to specific cells or defined cell populations. In particular the invention provides millisecond-timescale temporal control of cation channels using moderate light intensities in cells, cell lines, transgenic animals, and humans. The invention provides for optically generating electrical spikes in nerve cells and other excitable cells useful for driving neuronal networks, drug screening, and therapy.

24 Claims, 14 Drawing Sheets

(56) References Cited

U.S. PATENT DOCUMENTS

| | | |
|---|---|---|
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,939,320 A | 8/1999 | Littman et al. |
| 6,057,114 A | 5/2000 | Akong |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2003/0009103 A1 | 1/2003 | Yuste et al. |
| 2003/0026784 A1 | 2/2003 | Koch et al. |
| 2003/0040080 A1* | 2/2003 | Miesenbock et al. ........ 435/69.1 |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0068202 A1 | 4/2004 | Hansson et al. |
| 2004/0076613 A1 | 4/2004 | Mazarakis et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0107753 A1 | 5/2005 | Rezai et al. |
| 2005/0119315 A1 | 6/2005 | Fedida et al. |
| 2005/0124897 A1 | 6/2005 | Chopra |
| 2005/0153885 A1 | 7/2005 | Yun et al. |
| 2005/0197679 A1 | 9/2005 | Dawson |
| 2005/0202398 A1* | 9/2005 | Hegemann et al. ............... 435/4 |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |

(56) References Cited

U.S. PATENT DOCUMENTS

| | | |
|---|---|---|
| 2008/0290318 A1 | 11/2008 | Van Veggel et al. |
| 2009/0030930 A1 | 1/2009 | Pradeep et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0234273 A1 | 9/2010 | Deisseroth et al. |
| 2011/0021970 A1 | 1/2011 | Vo-Dinh et al. |
| 2011/0092800 A1 | 4/2011 | Yoo et al. |
| 2011/0105998 A1 | 5/2011 | Deisseroth et al. |
| 2011/0112179 A1 | 5/2011 | Deisseroth et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0144359 A1 | 6/2013 | Kishawi et al. |

FOREIGN PATENT DOCUMENTS

| | | |
|---|---|---|
| WO | WO 03-040323 | 5/2003 |
| WO | WO 03-084994 | 10/2003 |
| WO | WO 03-102156 | 12/2003 |
| WO | WO 2004/033647 | 4/2004 |
| WO | WO 2007-024391 | 3/2007 |
| WO | WO 2007-131180 | 11/2007 |
| WO | WO 2008/086470 | 7/2008 |
| WO | WO 2008/106694 | 9/2008 |
| WO | WO 2009/025819 | 2/2009 |
| WO | WO2009/119782 | 10/2009 |
| WO | WO 2009-131837 | 10/2009 |
| WO | WO 2010/011404 A3 | 1/2010 |
| WO | WO 2010/056970 | 5/2010 |
| WO | WO-2010123993 | 10/2010 |
| WO | WO 2011/066320 A3 | 6/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/126521 | 8/2013 |
| WO | WO 2013/142196 | 9/2013 |

OTHER PUBLICATIONS

Lanyi et al. "The primary structure of a Halorhodopsin from *Natronobacterium pharaonis*" Journal of Biological Chemistry 1990, vol. 265, No. 3, p. 1253-1260.

Hofherr et al. "Selective Golgi export of Kir2.1 controls the stoichiometry of functional Kir2.x channel heteromers" Journal of Cell Science, 2005, vol. 118, p. 1935-1943.

Loetterle, et al., "Cerebellar Stimulation: Pacing the Brain", American Journal of Nursing, 1975, vol. 75, No. 6, pp. 958-960.

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.

Han, et al., "Multiple-Color Optical Activation, Silencing, and Desynchronization of Neural Activity with Single-Spike Temporal Resolution", PLoS One, 2007, vol. 2, No. 3, pp. 1-12.

Kinoshita, et al., "Optogenetically Induced Supression of Neural Activity in the Macaque Motor Cortex", Poster Sessions Somatomotor System, Others,2010, pp. 141-154.

Rein, et al., "The Optogenetic (r)evolution", Mol. Genet. Genomics, 2012, vol. 287, No. 2, pp. 95-109.

Remy, et al., "Depression in Parkinson's Disease: Loss of Dopamine and Noradrenaline Innervation in the Limbic System", Brain, 2005, vol. 128 (Pt 6), pp. 1314-1322.

Tsai, et al., "Phasic Firing in Dopaminergic Neurons in Sufficient for Behavioral Conditioning", Science, 2009, vol. 324, pp. 1080-1084.

Zhao, et al., "Improved Expression of Halorhodopsin for Light-Induced Silencing of Neuronal Activity", Brain Cell Biology, 2008, vol. 36 (1-4), pp. 141-154.

Balint, et al., "The Nitrate Transporting Photochemical Reaction Cycle of the Pharaonis Halorhodopsin", Biophysical Journal, 2004, vol. 86, pp. 1655-1663.

Cazillis et al., "VIP and PACAP induce selective neuronal differentiation of mouse embryonic stem cells", Eur J Neurosci, 2004, 19(4):798-808.

Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.

Aebischer, et al. "Long-Term Cross-Species Brain Transplantation of a Polymer-Encapsulated Dopamine-Secreting Cell Line", Experimental Neurology, 1991, vol. 111, pp. 269-275.

Ahmad, et al. "The *Drosophila rhodopsin* cytoplasmic tail domain is required for maintenance of rhabdomere structure." The FASEB Journal, 2007, vol. 21, p. 449-455.

Airan, et al., "Temporally Precise in vivo Control of Intracellular Signaling", 2009, Nature, vol. 458, No. 7241, pp. 1025-1029.

Akirav, et al. "The role of the medial prefrontal cortex-amygdala circuit in stress effects on the extinction of fear", Neural Plasticity, 2007: vol. 2007 Article ID:30873, pp. 1-11.

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Argos, et al. "The integrase family of site-specific recombinases: regional similarities and global diversity", The EMBO Journal, 1986, vol. 5, No. 2, pp. 433-440.

Bamberg et al. "Light-driven proton or chloride pumping by halorhodopsin." Proc. Natl. Academy Science USA, 1993, vol. 90, no. 2, p. 639-643.

Banghart, et al. "Light-activated ion channels for remote control of neuronal firing". Nature Neuroscience, 2004, vol. 7, No. 12 pp. 1381-1386.

Basil et al. "Is There Evidence for Effectiveness of Transcranial Magnetic Stimulation in the Treatment of Psychiatric Disorders?" Psychiatry, 2005, pp. 64-69.

Bebbington et al., "The use of vectors based on gene amplification for the expression of cloned genes in mammalian cells in DNA cloning" vol. 3, Academic Press, New York, 1987.

Benabid "Future strategies to restore brain functions," Conference proceedings from Medicine Meets Millennium: World Congress of Medicine and Health, 2000, 6 pages.

(56) References Cited

OTHER PUBLICATIONS

Benoist et al. "In vivo sequence requirements of the SV40 early promotor region" Nature (London), 1981, vol. 290(5804): pp. 304-310.

Berges et al., "Transduction of Brain by Herpes Simplex Virus Vectors", Molecular Therapy, 2007, vol. 15, No. 1: pp. 20-29.

Berridge et al., "The Versatility and Universality of Calcium Signaling", Nature Reviews: Molecular Cell Biology, 2000, vol. 1: pp. 11-21.

Bocquet et al. "A prokaryotic proton-gated ion channel from the nicotinic acetylcholine receptor family." Nature Letters, 2007, vol. 445, p. 116-119.

Boyden, et al. "Millisecond-timescale, genetically targeted optical control of neural activity" Nature Neuroscience, 2005, vol. 8, No. 9: pp. 1263-1268.

Bi, et al. "Ectopic Expression of a Microbial-Type Rhodopsin Restores Visual Responses in Mice with Photoreceptor Degeneration", Neuron, 2006, vol. 50, No. 1: pp. 23-33.

Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.

Blomer et al., "Highly Efficient and Sustained Gene Transfer in Adult Neurons with Lentivirus Vector", Journal of Virology,1997, vol. 71, No. 9: pp. 6641-6649.

Braun, "Two Light-activated Conductances in the Eye of the Green Alga Volvox carteri", 1999, Biophys J., vol. 76, No. 3, pp. 1668-1678.

Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.

Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.

Brown, et al. "Long-term potentiation induced by θ frequency stimulation is regulated by a protein phosphate-operated gate." The Journal of Neuroscience, 2000, vol. 20, No. 21, pp. 7880-7887.

Callaway, et al. "Photostimulation using caged glutamate reveals functional circuitry in living brain slices", Proc. Natl. Acad. Sci. USA., 1993, vol. 90: pp. 7661-7665.

Campagnola et al. "Fiber-coupled light-emitting diode for localized photostimulation of neurons expressing channelrhodopsin-2." Journal of Neuroscience Methods, 2008, vol. 169, Issue 1. Abstract only.

Cardin, et al. "Driving Fast spiking Cells Induces Gamma Rhythm and Controls Sensory Responses", 2009, Nature, vol. 459, vol. 7247, pp. 663-667.

Cenatiempo "Prokaryotic gene expression in vitro: transcription-translation coupled systems", Biochimie, 1986, vol. 68(4): pp. 505-515.

Claudio et al. "Nucleotide and deduced amino acid sequences of *Torpedo californica* acetylcholine receptor gamma subunit." PNAS USA,1983, vol. 80, p. 1111-1115.

Collingridge et al. "Inhibitory post-synaptic currents in rat hippocampal CA1 neurones." J. Physiol., 1984, vol. 356, pp. 551-564.

Covington, et al. "Antidepressant Effect of Optogenetic Stimulation of the Medial Prefrontal Cortex." Journal of Neuroscience, 2010, vol. 30(48), pp. 16082-16090.

Crouse, et al. "Expression and amplification of engineered mouse dihydrofolate reductase minigenes" Mol. Cell. Biol., 1983, vol. 3(2): pp. 257-266.

Cucchiaro et al., "*Phaseolus vulgaris* leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

Cucchiaro et al., "Electron-Microsoft Analysis of Synaptic Input from the Perigeniculate Nucleus to A-Lamine of the Lateral Geniculate Nucleus in Cats", The Journal of Comparative Neurology, 1991, vol. 310, pp. 316-336.

Cui, et al., "Electrochemical deposition and characterization of conducting polymer polypyrrole/PSS on multichannel neural probes," Sensors and Actuators, 2001, vol. 93(1): pp. 8-18.

Date, et al. "Grafting of Encapsulated Dopamine-Secreting Cells in Parkinson's Disease: Long-Term Primate Study", Cell Transplant, 2000, vol. 9, pp. 705-709.

Dalva, et al. "Rearrangements of Synaptic Connections in Visual Cortex Revealed by Laser Photostimulation", Science, 1994,vol. 265, pp. 255-258.

Dederen, et al. "Retrograde neuronal tracing with cholera toxin B subunit: comparison of three different visualization methods", Histochemical Journal, 1994, vol. 26, pp. 856-862.

De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.

Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.

Deisseroth et al., "Translocation of Calmodulin to the Nucleus Supports CREB Phosphorylation in Hippocampal Neurons", Nature, 1998, vol. 392, pp. 198-202.

Deisseroth et al., "Signaling from Synapse to Nucleus: the logic Behind the Mechanisms", Currrent Opinion in Neurobiology, 2003, vol. 13, pp. 354-365.

Deisseroth et al., "Excitation-neurogenesis Coupling in Adult Neural Stem/Progenitor Cells", 2004, Neuron, vol. 42, pp. 535-552.

Deisseroth "Next-generation optical technologies for illuminating genetically targeted brain circuits," The Journal of Neuroscience, 2006, vol. 26, No. 41, pp. 10380-10386.

Denk, W., et al. "Anatomical and functional imaging of neurons using 2-photon laser scanning microscopy", Journal of Neuroscience Methods, 1994, vol. 54, pp. 151-162.

Ditterich, et al. "Microstimulation of visual cortex affects the speed of perceptual decisions", 2003, Nature Neuroscience, vol. 6, No. 8, pp. 891-898.

Dittgen, et al. "Lentivirus-based genetic manipulations of cortical neurons and their optical and electrophysiological monitoring in vivo", PNAS, 2004, vol. 101, No. 52, pp. 18206-18211.

Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.

Ensell, et al. "Silicon-based microelectrodes for neurophysiology, micromachined from silicon-on-insulator wafers," Med. Biol. Eng. Comput., 2000, vol. 38, pp. 175-179.

Eisen, "Treatment of amyotrophic lateral sclerosis", Drugs Aging, 1999; vol. 14, No. 3, pp. 173-196.

Ernst, et al. "Photoactivation of Channelrhodopsin", 2008, vol. 283, No. 3, pp. 1637-1643.

Esposito et al. "The integrase family of tyrosine recombinases: evolution of a conserved active site domain", Nucleic Acids Research, 1997, vol. 25, No. 18, pp. 3605-3614.

Fabian et al. "Transneuronal transport of lectins" Brain Research, 1985, vol. 344, pp. 41-48.

Falconer et al. "High-throughput screening for ion channel modulators," Journal of Biomolecular Screening, 2002, vol. 7, No. 5, pp. 460-465.

Farber, et al. "Identification of Presynaptic Neurons by Laser Photostimulation", Science, 1983, vol. 222, pp. 1025-1027.

Feng, et al. "Imaging Neuronal Subsets in Transgenic Mice Expressing Multiple Spectral Variants of GFP", Neuron, 2000, vol. 28, pp. 41-51.

Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.

Fitzsimons et al., "Promotors and Regulatory Elements that Improve Adeno-Associated Virus Transgene Expression in the Brain", 2002, Methods, vol. 28, pp. 227-236.

Foster, "Bright blue times", Nature, 2005, vol. 433, pp. 698-699.

Genbank Accession No. DQ094781 (Jan. 15, 2008).

Gelvich et al. "Contact flexible microstrip applicators (CFMA) in a range from microwaves up to short waves," IEEE Transactions on Biomedical Engineering, 2002, vol. 49, Issue 9: 1015-1023.

(56) References Cited

OTHER PUBLICATIONS

Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation-a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat", Neuroscience, 1997, vol. 76, No. 3, pp. 689-706.
Gottesman et al. "Bacterial regulation: global regulatory networks," Ann. Rev. Genet., 1984, vol. 18, pp. 415-441.
Gradinaru, et al. "ENpHR: a *Natronomonas* Halorhodopsin Enhanced for Optogenetic Applications", 2008, Brain Cell Biol., vol. 36 (1-4), pp. 129-139.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol., 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J., 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kandel, E.R., et al. "Electrophysiology of Hippocampal Neurons: I. Sequential Invasion and Synaptic Organization," J Neurophysiol, 1961, vol. 24, pp. 225-242.
Kandel, E.R., et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of *Volvox carteri* are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-10.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.

(56) References Cited

OTHER PUBLICATIONS

Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1 K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of *FRT* sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5. 1-09.5.19.
Nacher, et al. "NMDA receptor antagonist treatment increases the production of newneurons in the aged rat hippocampus", Neurobiology of Aging, 2003, vol. 24, No. 2: pp. 273-284.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration,"Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.

(56) References Cited

OTHER PUBLICATIONS

Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Rathnasingham et al., "Characterization of implantable microfabricated fluid delivery devices," IEEE Transactions on Biomedical Engineering, 2004, vol. 51, No. 1: pp. 138-145.
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sajdyk, et al., "Excitatory Amino Acid Receptors in the Basolateral Amygdala Regulate Anxiety Responses in the Social Interaction Test", Brain Research, 1997, vol. 764, pp. 262-264.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast *GAL4* gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of Tea on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye. et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Tye, et al. "Optogenetic investigation of neural circuits underlying brain disease in animal models," Nature Reviews Neuroscience (Mar. 2012), 13(4):251-266.
"SubName: Full=Channelrhodopsin-1", retrieved from EBI accession No. UNIPROT: B4Y103. Database accession No. B4Y103. Sep. 23, 2008.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.

(56) References Cited

OTHER PUBLICATIONS

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.
Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β, β-Carotene-15, 15'Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"*N. pharaonis* halorhodopsin (hop) gene, complete cds.", XP002704883, retrieved from EBI accession No. EMBL: J05199. Database accession No. J05199. Nov. 22, 1990.
"Subname: Fluu=Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia" Psychopharmacology, 2010, 211:355-366.
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila* larvae", Current Biology, Sep. 2006, 16(17):1741-1747.
appetitive or aversive learning in drosophila larvae, Current Biology, Sep. 2006, 16(17):1741-1747.
Gradinaru et al., "Targeting and readout strategies for fast optical neural control in vitro and in vivo", J Neuroscience, 2007, 27(52):14231-14238.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
U.S. Appl. No. 13/622,809, filed Sep. 19, 2012, Deisseroth, et al.
U.S. Appl. No. 13/623,612, filed Sep. 20, 2012, Deisseroth, et al.
U.S. Appl. No. 13/718,243, filed Dec. 18, 2012, Deisseroth, et al.
U.S. Appl. No. 13/763,119, filed Feb. 8, 2013, Deisseroth, et al.
U.S. Appl. No. 13/763,132, filed Feb. 8, 2013, Deisseroth, et al.
U.S. Appl. No. 13/772,732, filed Feb. 21, 2013, Deisseroth, et al.
U.S. Appl. No. 13/847,653, filed Mar. 20, 2013, Deisseroth, et al.
U.S. Appl. No. 13/847,785, filed Mar. 20, 2013, Deisseroth, et al.
U.S. Appl. No. 13/849,913, filed Mar. 25, 2013, Deisseroth, et al.
U.S. Appl. No. 13/850,426, filed Mar. 26, 2013, Deisseroth, et al.
U.S. Appl. No. 13/850,428, filed Mar. 26, 2013, Deisseroth, et al.
U.S. Appl. No. 13/850,436, filed Mar. 26, 2013, Deisseroth, et al.
U.S. Appl. No. 13/850,709, filed Mar. 26, 2013, Deisseroth, et al.
U.S. Appl. No. 13/854,750, filed Apr. 1, 2013, Deisseroth, et al.
U.S. Appl. No. 13/854,754, filed Apr. 1, 2013, Deisseroth, et al.
U.S. Appl. No. 13/855,413, filed Apr. 2, 2013, Deisseroth, et al.
U.S. Appl. No. 13/875,966, filed May 2, 2013, Deisseroth, et al.
U.S. Appl. No. 13/882,566, filed Nov. 4, 2011, Deisseroth, et al.
U.S. Appl. No. 13/882,666, filed Nov. 4, 2011, Deisseroth, et al.
U.S. Appl. No. 13/882,670, filed Nov. 4, 2011, Deisseroth, et al.
U.S. Appl. No. 13/882,703, filed Nov. 4, 2011, Deisseroth, et al.
U.S. Appl. No. 13/882,705, filed Nov. 4, 2011, Deisseroth, et al.
U.S. Appl. No. 13/882,719, filed Nov. 4, 2011, Deisseroth, et al.

(56) References Cited

OTHER PUBLICATIONS

Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Xiong et al., "Interregional connectivity to primary motor cortex revealed using MRI resting state images", Hum Brain Mapp, 1999, 8(2-3):151-156.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004, pp. 750-769.
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496 (7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491 (7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9 (4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8(8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Evanko "Optical excitation yin and yang" Nature Methods, 2007, 4:384.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
Delaney et al., "Evidence for a long-lived 13-cis-containing intermediate in the photocycle of the leu 93→ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.

(56) References Cited

OTHER PUBLICATIONS

Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.

Pinkham et al., "Neural bases for impaired social cognition in schizophrenia and autism spectrum disorders", Schizophrenia Research, 2008, vol. 99, pp. 164-175.

Sohal et al., "Parvalbumin neurons and gamma rhythms enhance cortical circuit performance", Nature, 2009, vol. 459, No. 7247, pp. 698-702.

Yizhar et al., "Optogenetics in neural systems", Neuron Primer, 2011, vol. 71, No. 1, pp. 9-34.

Li et al., "Surface Expression of Kv1 Channels is Governed by a C-Terminal Motif", J. Bioi. Chem. (2000), 275(16):11597-11602.

Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.

Varo et al.,"Light-Driven Chloride Ion Transport by Halorhodopsin from *Natronobacterium pharaonis*. 2. Chloride Release and Uptake, Protein Conformation Change, and Thermodynamics", Biochemistry (1995), 34(44):14500-14507.

Deisseroth, et al., "Controlling the Brain with Light", Scientific American, 2010, vol. 303, pp. 48-55.

Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.

Sineshchekov, et al., "Two Rhodopsins Mediate Phototaxis to Low and High Intensity Light in *Chlamydomas reinhardtii*", PNAS, 2002, vol. 99, No. 13, pp. 8689-8694.

Tønnese, et al., "Optogenetic Control of Epileptiform Activity", PNAS, 2009, vol. 106, No. 29, pp. 12162-12167.

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Cowan et al., "Targeting gene expression to endothelium in transgenic animals: a comparison of the human ICAM-2, PECAM-1, and endoglin promoters", Xenotransplantation, 2003, vol. 10, pp. 223-231.

Definition of Psychosis (2015).

Ebert et al., "A Moloney MLV-rat somatotropin fusion gene produces biologically active somatotropin in a transgenic pig", Mol. Endocrinology, 1988, vol. 2, pp. 277-283.

Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.

Karra, et al. "Transfection Techniques for Neuronal Cells", The Journal of Neuroscience, 2010, vol. 30, No. 18, pp. 6171-6177.

Kelder et al., "Glycoconjugates in human and transgenic animal milk", Advances in Exp. Med. And Biol., 2001, vol. 501, pp. 269-278.

Mullins et al., "Fulminant hypertension in transgenic rats harbouring the mouse *Ren-2* gene", Nature, 1990, vol. 344, pp. 541-544.

Mullins et al., "Expression of the DBA/2J *Ren-2* gene in the adrenal gland of transgenic mice", EMBO, 1989, vol. 8, pp. 4065-4072.

Taurog et al., "HLA-B27 in inbred and non-inbred transgenic mice", J. Immunol., 1988, vol. 141, pp. 4020-4023.

Wall, "Transgenic livestock: Progress and prospects for the future", Theriogenology, 1996, vol. 45, pp. 57-68.

Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.

Written opinion of PCT Application No. PCT/US2011/059383 (May 9, 2012).

\* cited by examiner

SEQ ID NO. 1

```
Met Asp Tyr Gly Gly Ala Leu Ser Ala Val Gly Arg Glu Leu Leu Phe
1               5                   10                  15
Val Thr Asn Pro Val Val Val Asn Gly Ser Val Leu Val Pro Glu Asp
            20                  25                  30
Gln Cys Tyr Cys Ala Gly Trp Ile Glu Ser Arg Gly Thr Asn Gly Ala
            35                  40                  45
Gln Thr Ala Ser Asn Val Leu Gln Trp Leu Ala Ala Gly Phe Ser Ile
        50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Glu Met Val Lys Val Ile Leu
                85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Cys
            115                 120                 125
Pro Val Ile Leu Ile His Leu Ser Asn Leu Thr Gly Leu Ser Asn Asp
        130                 135                 140
Tyr Ser Arg Arg Thr Met Gly Leu Leu Val Ser Asp Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
            195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
        290                 295                 300
Glu Ala Gly Ala Val Pro
305                 310
```

FIG. 12

SEQ ID NO. 2

```
atggattatg gaggcgccct gagtgccgtt gggcgcgagc tgctatttgt aacgaaccca   60
gtagtcgtca atggctctgt acttgtgcct gaggaccagt gttactgcgc gggctggatt  120
gagtcgcgtg gcacaaacgg tgcccaaacg gcgtcgaacg tgctgcaatg gcttgctgct  180
ggcttctcca tcctactgct tatgttttac gcctaccaaa catggaagtc aacctgcggc  240
tgggaggaga tctatgtgtg cgctatcgag atggtcaagg tgattctcga gttcttcttc  300
gagtttaaga acccgtccat gctgtatcta gccacaggcc accgcgtcca gtggttgcgt  360
tacgccgagt ggcttctcac ctgcccggtc attctcattc acctgtcaaa cctgacgggc  420
ttgtccaacg actacagcag gcgcaccatg ggtctgcttg tgtctgatat tggcacaatt  480
gtgtggggcg ccacttccgc catggccacc ggatacgtca aggtcatctt cttctgcctg  540
ggtctgtgtt atggtgctaa cacgttcttt cacgctgcca aggcctacat cgagggttac  600
cacaccgtgc cgaagggccg tgtcgccag gtggtgactg catggcttg gctcttcttc  660 gtatcatggg gtatgttccc catcctgttc atcctcggcc ccgagggctt cggcgtcctg  720
agcgtgtacg gctccaccgt cggccacacc atcattgacc tgatgtcgaa gaactgctgg  780
ggtctgctcg ccactacct gcgcgtgctg atccacgagc atatcctcat ccacggcgac  840
attcgcaaga ccaccaaatt gaacattggt ggcactgaga ttgaggtcga cgctggtg   900 gaggacgagg ccgaggctgg cgcggtaccc                                   930
```

FIG. 13

SEQ ID NO. 3

```
atggactatg cggcgcttt gtctgccgtc ggacgcgaac ttttgttcgt tactaatcct  60
gtggtggtga acgggtccgt cctggtccct gaggatcaat gttactgtgc cggatggatt 120
gaatctcgcg gcacgaacgg cgctcagacc gcgtcaaatg tcctgcagtg gcttgcagca 180
ggattcagca ttttgctgct gatgttctat gcctaccaaa cctggaaatc tacatgcggc 240
tgggaggaga tctatgtgtg cgccattgaa atggttaagg tgattctcga gttctttttt 300
gagtttaaga tccctctat gctctacctt gccacaggac accgggtgca gtggctgcgc 360
tatgcagagt ggctgctcac ttgtcctgtc atccttatcc acctgagcaa cctcaccggc 420
ctgagcaacg actacagcag gagaaccatg ggactccttg tctcagacat cgggactatc 480
gtgtgggggg ctaccagcgc catggcaacc ggctatgtta aagtcatctt cttttgtctt 540
ggattgtgct atggcgcgaa cacatttttt cacgccgcca agcatatat cgagggttat 600
catactgtgc caaagggtcg gtgccgccag gtcgtgaccg gcatggcatg gctgttttc 660
gtgagctggg gtatgttccc aattctcttc attttggggc ccgaaggttt tggcgtcctg 720
agcgtctatg gctccaccgt aggtcacacg attattgatc tgatgagtaa aaattgttgg 780
gggttgttgg gacactacct gcgcgtcctg atccacgagc acatattgat tcacggagat 840
atccgcaaaa ccaccaaact gaacatcggc ggaacggaga tcgaggtcga gactctcgtc 900
gaagacgaag ccgaggccgg agccgtgcca                                    930
```

FIG. 14

LIGHT-ACTIVATED CATION CHANNEL AND USES THEREOF

CROSS-REFERENCE

This application is related to and claims priority to U.S. Provisional Application No. 60/701,799, filed Jul. 22, 2005, which is incorporated herein by reference in its entirety.

STATEMENT AS TO FEDERALLY SPONSORED RESEARCH

This invention was made with Government support under contracts DC007006 and MH071315 awarded by the National Institutes of Health. The Government has certain rights in the invention.

FIELD OF THE INVENTION

The invention relates to light-activated ion channel proteins that can generate millisecond-timescale electrical spikes when incorporated into neurons and illuminated with rapid pulses of light. In particular the invention provides millisecond-timescale temporal control of cation channels using moderate light intensities in cells, cell lines, transgenic animals, and humans. The invention is useful for driving neuronal networks, for drug screening, and for therapy.

BACKGROUND OF THE INVENTION

Ion channel proteins control the flow of ions across membranes, for instance, between the cytoplasm and the outside of a cell. A cation channel operates by controlling the flow of cations such as sodium, potassium, calcium, lithium, rubidium, and cesium. When the cation channel is closed, the transport of cations across the membranes is slow, when the cation channel opens, the flow of cations through the channel increases. If the opening of the channel results in a net flow of cations to one side of the membrane, an electrical current will be generated. The flow of ions across the membrane can also result in a change in the voltage across the membrane. If there is a net voltage across the membrane at the time the channel is opened, cations will tend to flow so as to cause depolarization of the membrane. Neurons (nerve cells) use rapid depolarizations to create action potentials (spikes) creating electrical signals that propagate down the neuron. These action potentials, nerve impulses, or spikes occur on the millisecond time scale, and they are the basis by which the neuron acts to signal, and control brain and muscle function.

Neurons receive, conduct, and transmit signals. In a motor neuron, the signals represent commands for the contraction of a particular muscle. In a sensory neuron, signals represent the information that a specific type of stimulus is present. In an interneuron, signals represent part of a computation that combines sensory information from many different sources and generates an appropriate set of motor commands in response. Communication depends on an electrical disturbance in one part of the membrane spreading to other parts of the cell. These communications are often via an action potential, also referred to as a spike or a nerve impulse. Neuronal signals are transmitted from cell to cell at synapses which are specialized sites of cell contact. Synapses can be either electrical synapses (gap junctions), or chemical synapses. The usual mechanism of communication across a chemical synapse involves a change in electrical potential within a first (presynaptic) neuron that results in the release of neurotransmitter. The neurotransmitter diffuses to a second (postsynaptic) neuron across the gap between the neurons (the synaptic cleft). The neurotransmitter can provoke an electrical response in the postsynaptic neuron. The change created at the synapse due to the electrical signal from the presynaptic neuron is a synaptic event. Synaptic events can be excitatory or inhibitory. By controlling synaptic events, the control of transmission of signals between neurons can be controlled, allowing optical driving of activity throughout a connected neural network.

Noninvasive temporal control of activity in defined neuronal populations is a long-sought goal of neuroscience. In the mammalian nervous system, it is believed that neural computation depends on the temporally diverse, precise spiking patterns of different classes of neurons, which express unique genetic markers and display heterogeneous morphological and wiring properties (e.g. Pouille et al., Nature 429: 717 (2004), Nirenberg et al., Neuron 18:637 (1997), Klausberger et al., Nature 421:844 (2003), Hausser et al., Neuron 19:665 (1997)) within connected networks. While direct field stimulation and recording of neurons in intact brain tissue have provided many insights into the causal function of circuit subfields (Kandel et al., J Neurophysiol 24:243 (1961), Kandel et al., J Neurophysiol 24:225 (1961), Ditterich et al., Nat Neurosci 6:891 (2003), Gold et al., Nature 404:390 (2000), Salzman et al., Nature 346:174 (1990), neurons belonging to a specific class are often sparsely embedded within dense tissue, posing fundamental challenges for resolving the causal role of particular neuron types in information processing.

For many cellular and systems neuroscience processes (and for nonspiking neurons in species like *C. elegans*), subthreshold depolarizations convey information of physiological significance. For example, subthreshold depolarizations are highly potent for activating synapse-to-nucleus signaling (Mermelstein et al., J. Neurosci. 20:266 (2000)), and the relative timing of subthreshold and suprathreshold depolarizations is critical for determining the sign of synaptic plasticity (Bi et al., J. Neurosci. 18:10464 (1998)). But compared with driving spiking, it is in principle a more difficult task to drive reliable and precisely sized subthreshold depolarizations. The sharp threshold for action potential production facilitates reliable spiking, while the all-or-none dynamics of spiking produces virtually identical waveforms from spike to spike, even in the presence of significant neuron-to-neuron variability in electrical properties. In contrast, subthreshold depolarizations, which operate in the linear regime of membrane voltage, will lack these intrinsic normalizing mechanisms.

Despite the progress made in the analysis of neural network geometry via non-cell type specific techniques like glutamate uncaging (e.g. Shepherd et al., Neuron 38:277 (2003), Denk et al., J Neurosci Methods 54:151 (1994), Pettit et al., J Neurophysiol 81:1424 (1999), Yoshimura et al., Nature 433: 868 (2005), Dalva et al., Science 265:255 (1994), Katz et al., J Neurosci Methods 54:205 (1994)), no non-invasive technology has yet been invented with the requisite spatiotemporal resolution to probe neural coding in specific neurons at the resolution of single spikes. Previously genetically-encoded optical methods, have demonstrated control of neuronal function only over timescales of seconds to minutes, perhaps due to the nature of their membrane potential control mechanisms. Kinetics roughly a thousand times faster would enable remote control of individual spikes or synaptic events. Thus, existing genetically-targeted approaches require expensive, custom-synthesized exogenous compounds, and operate on the scale of seconds to minutes (Lima et al., Cell 121:141 (2005), Banghart et al., Nat Neurosci 7:1381 (2004), Zemelman et al., Proc Natl Acad Sci USA 100:1352 (2003), Foster et al., Nature 433:698 (2005)).

Thus, compositions and methods for higher-temporal resolution, noninvasive, and genetically-based control of neural activity would be desirable.

SUMMARY OF THE INVENTION

Accordingly, one aspect of the invention provides for compositions and methods related to light-activated cation channel (LACC) proteins with millisecond-scale opening kinetics that provide genetically targeted photostimulation at fine temporal resolution, enabling elucidation of the temporal activity patterns in specific neurons that suffice to drive circuit dynamics, information processing, and plasticity. The composition and methods herein offer optical control of the electrical and ionic milieu of neurons and a variety of other cell types, both in vitro and in vivo, at the rapid timescales important for many biological processes—including ion channel modulation, signal transduction, neural coding via temporal spiking and synaptic activation patterns, sensory and motor processing, interneuron modulation of circuit dynamics, and neuropsychiatric dysfunction. Additional aspects of the invention include compositions and methods relating to light-activated cation channel proteins for drug discovery and biotechnological and neuropsychiatric applications, advancing the ability to characterize, detect, and treat a variety of medical disorders.

Another aspect of the present invention is a composition comprising a light-activated cation channel protein that is expressed in a cell wherein the cell is selected from the group consisting of mammalian cells, neurons, and stem cells. In one embodiment, the light-activated cation channel protein is ChR2, Chop2, ChR2-310, or Chop2-310. In another embodiment, the light-activated cation channel protein is a 7-transmembrane protein. In another embodiment, the light-activated cation channel protein is a single-component protein. In yet another embodiment, the LACC protein covalently binds retinal.

Still another aspect of the present invention is an isolated LACC protein that responds to a light stimulus within 1 ms.

Another aspect of the present invention is an isolated LACC protein that generates a stable photocurrent that does not increase or decrease by about 10% over about 60 min.

Another aspect of the present invention is an isolated LACC protein that generates electrical responses with a temporal jitter of less than about 5 ms.

Another aspect of the present invention is an isolated LACC protein that can generate subthreshold pulses with a coefficient of variation of less than about 0.2 over about 5 pulses.

Another aspect of the present invention is a nucleic acid sequence comprising a gene for LACC protein and a promoter. In one embodiment, the promoter is a cell specific promoter. In another embodiment, the promoter is a promoter for somatostatin, parvalbumin, GABAα6, L7, or calbindin. In another embodiment, the promoter is a cell general purpose promoter. In another embodiment, the promoter is EF1-alpha. In another embodiment, the nucleic acid sequence comprises a bacterial artificial chromosome (BAC). In another preferred embodiment, the promoter is an inducible promoter, such as a promoter inducible by a trans-acting factor which can respond to an administered drug.

Another aspect of the present invention is a fusion protein comprising a LACC protein coupled to another functional protein. In one embodiment, the other functional protein is a fluorescent protein. In one embodiment, the other functional protein is mCherry, GFP, YFP, or CFP. In one embodiment, the other functional protein targets a subcellular region. In one embodiment, the other functional protein has a PDZ or AIS domain.

Another aspect of the present invention is a vector for delivering a LACC protein comprising; a nucleic acid sequence that codes for LACC protein and a promoter. In one embodiment the vector comprises a virus. A preferred embodiment of a virus is a lentivirus or retrovirus.

Another aspect of the present invention is a cell that expresses a LACC protein. In one embodiment, the cell is a mammal cell, a stem cell, or a neuron.

Another aspect of the present invention is a cell line that expresses a LACC protein. In one embodiment, the cell line is a mammal cell line, a stem cell line, or a neuronal cell line.

Another aspect of the present invention is a transgenic animal that expresses a LACC protein. In one embodiment, the transgenic animal is a fly, worm, mouse, or zebrafish.

Another aspect of the present invention is a method of optically controlling cell properties comprising; causing the cell to express light activated cation channel protein; and exposing the cell to light to activate the LACC protein. In one preferred embodiment, the exposing of the cell to light creates an electrical response in the cell. In another preferred embodiment, the activation of the LACC protein causes the release of a peptide (e.g. insulin, leptin, neuropeptide Y, substance P, human growth hormone, secretin, glucagon, endorphin, oxytocin, vasopressin, or orexin/hypocretin). In another preferred embodiment, the activation of the LACC protein causes the release of a small molecule whose synthesis or release is dependent on cell electrical activity (e.g., nitric oxide, or a cannabinoid such as anandamide or 2-arachidonylglycerol (2-AG)). In another preferred embodiment of the invention, the activation of the LACC protein causes the release of a cytokine. In another preferred embodiment of the invention, the cell causes a muscle cell, and the activation of the LACC protein comprises causing the muscle cell to contract Another aspect of the present invention is a method of controlling synaptic transmissions comprising; causing a neuron that ends in a synapse to express a LACC protein; and exposing the neuron to light to activate the LACC protein, wherein the exposing to light causes a synaptic event. In one embodiment, the synaptic event creates a synaptic transmission. In another embodiment, the synaptic transmission transmits a signal to a second neuron. In another embodiment, the synaptic transmission drives activity through a connected neural network. In an embodiment, the synaptic event is excitatory or inhibitory. In yet another embodiment, the synaptic event comprises the release of a small-molecule neuromodulator such as norepinephrine, serotonin, dopamine, acetylcholine, D-serine, histamine, or other small molecules that modulate cellular function.

Another aspect of the present invention is a method for targeted delivery of light-activated cation-channel proteins to specific cells comprising; contacting said cells with a vector comprising a nucleic acid sequence comprising a LACC protein wherein said vector selectively targets specific cells.

Another aspect of the present invention is a method for targeted delivery of light-activated cation-channel proteins to specific cells comprising; contacting said cells with a vector comprising a nucleic acid sequence comprising a LACC protein and a cell specific promoter, wherein said specific cells express said LACC protein.

Another aspect of the present invention is a method for screening for drugs comprising; expressing a LACC protein in a group of cells; exposing said group of cells to a compound that may have an effect on the cells; exposing said groups of cells to light; and monitoring the electrical response of cells within the group of cells to determine whether or not the compound has an effect on the cells. In a preferred embodiment, the monitoring of electrical response comprises optical imaging of fluorescence changes.

Another aspect of the present invention is a method for treating a subject comprising; delivering a vector comprising a LACC protein to excitable cells within the subject; and exposing said cells to light to affect such excitable cells.

Another aspect of the present invention is a method of controlling the behavior of an organism comprising;
delivering a vector comprising a LACC protein to cells within the organism; and
exposing said cells to light to control the organism's behavior.

Another aspect of the present invention is a method of stimulating subsets of nerve cells in the presence of other nerve cells comprising; exposing a group of nerve cells to a vector capable of genetically targeting a subset of the group of cells; and exposing the cells to light to activate the LACC protein in the subset of cells.

Another aspect of the present invention is method of driving differentiation in cells comprising: causing cells to express a LACC protein; and exposing the cells to light to activate the LACC protein, wherein the activation of the LACC protein drives differentiation of the progeny of the exposed cells. In a preferred embodiment, the cells comprise stem cells.

In preferred embodiments described herein, the light-activated cation channel protein is coded by a sequence of SEQ ID No. 2 or SEQ ID No. 3.

Another aspect of the invention is a method of treating a subject comprising administering to a patient in need thereof a therapeutically effective amount of a light activated cation channel protein. The methods described herein can be used for therapeutic and/or prophylatic benefit. Preferably the light activated cation channel is administered either in the form of a cell, the cell expressing a light activated cation channel protein or in the form of a vector comprising a nucleic acid sequence coding a light-activated cation channel protein, wherein the administration of the vector causes the expression of the light activated cation channel protein in a cell in said patient. Preferably, the light-activated cation channel protein is coded by a sequence of SEQ ID No. 2 or SEQ ID No. 3. In preferred embodiments the activation of the light-activated cation channel protein with light causes a release of a peptide, such as insulin, leptin, neuropeptide Y, substance P, human growth hormone, secretin, glucagon, endorphin, oxytocin, vasopressin, orexin/hypocretin, or a combination thereof. The activation of the light-activated cation channel protein can also cause release of a small molecule, such as nitric oxide or a cannabinoid. Also, the activation of the light-activated cation channel protein can cause release of a cytokine. In some embodiments, the light activated cation channel is expressed in a muscle cell and activation of the light-activated cation channel protein causes the muscle cell to contract. In other embodiments, the light activated cation channel is expressed in a neuronal cell and activation of the light-activated cation channel protein causes a synaptic event. The synaptic event can cause the release of a small-molecule neuromodulator, such as norepinephrine, serotonin, dopamine, acetylcholine, D-serine, histamine, or a combination thereof. The synaptic event can be excitatory or inhibitory. The light activated cation channel can be expressed in a stem cell, such as human embryonic stem cell, and activation of the light-activated cation channel protein can cause the stem cell to differentiate. The light activated cation channel is expressed in a cancer cell and activation of the light-activated cation channel protein causes a modulation of replication, survival, and/or controlled death in said cancer cell. Preferably, the light-activated cation channel protein is ChR2, Chop2, ChR2-310, or Chop2-310. An embodiment of an in vivo or ex vivo method comprises expressing a light activated cation channel protein in a stem cell, where said light activated cation channel protein is activated by exposure to light and said activation causes a modulation of replication said stem cell. In preferred embodiments, the light activated cation channel is expressed in retinal ganglion cells or spinal ganglion cells. A preferred embodiment is prosthetic devices, i.e., cells for implantation which express light activated cation channel. Preferred prosthetics are for the eyes or ears and preferably express ChR2, Chop2, ChR2-310, or Chop2-310. Preferably, the light activated cation channel protein is coded by a sequence of SEQ ID No. 2 or SEQ ID No. 3.

Yet another preferred aspect is a method of predicting potential ion channel modulating properties of a drug comprising: (a) expressing a light-activated cation channel protein and an ion channel of interest in a cell; (b) exposing said cell to light and monitoring a first response in said cell; (c) exposing said cell to a candidate drug; (d) further exposing said cell to light and monitoring a second response in said cell; and (e) determining an ion channel modulating property of said candidate drug based on a comparison of said first and second response. The monitoring of the responses can comprise optical imaging of changes in fluorescence in said cell or monitoring a signal transduction pathway. The signal transduction pathway can be monitored with an antibody, fluorescent small molecule, or a genetically encoded indicator. Preferably the light-activated cation channel protein is ChR2, Chop2, ChR2-310, or Chop2-310. Preferably, the light-activated cation channel protein is coded by a sequence of SEQ ID No. 2 or SEQ ID No. 3.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12 illustrates SEQ ID. No. 1.

FIG. 13 illustrates SEQ ID. No. 2.

FIG. 14 illustrates SEQ ID. No. 3.

DETAILED DESCRIPTION OF THE INVENTION

Figure 1A:
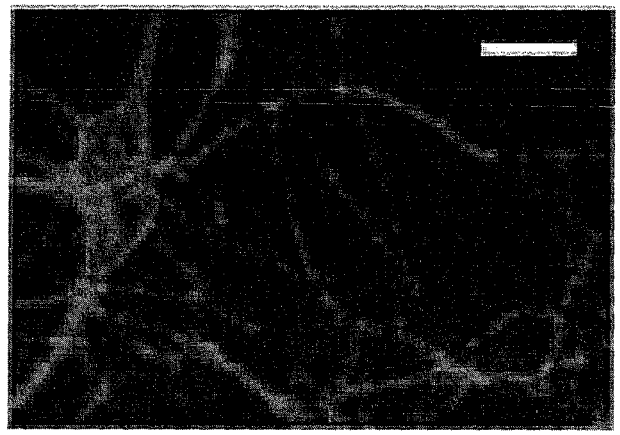
FIG. 1(a) shows a micrograph of hippocampal neurons expressing ChR2-YFP.

The present invention provides novel compositions and methods for controlling the electrical and chemical properties of cell membranes using light. The present invention also provides for a noninvasive, genetically targeted, high temporal resolution control of membrane electrical and chemical properties.

LACC

In a preferred embodiment of the invention, the light-activated cation channel protein comprises a 7-transmembrane protein.

In a preferred embodiment of the invention, the LACC comprises the protein, or portions of the protein Channelrhodopsin-2 (ChR2). ChR2 is a rhodopsin derived from the unicellular green alga *Chlamydomonas reinhardtii*. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2) (Nagel, et. al. Proc. Natl. Acad. Sci. USA 100:13940, and references cited therein). The LACC protein of the present invention can incorporate retinal that is added to the system, or, depending on the cell type that is used, background levels of retinal present in the cell may produce the required retinal. It is intended herein that the methods of the invention encompass either the opsin or the rhodopsin form of the LACC protein, e.g. Chop2 or ChR2. Typically, Chop2 and ChR2 can be interconverted by the addition or removal of the cofactor. Thus, as used herein, a LACC protein comprises an opsin with or without a co-factor. For example, as used herein, where a nucleic acid codes for an opsin protein such as Chop2, it codes for a light activated cation channel protein such as ChR2. Additionally, as used herein, where a cell expresses an opsin protein such as Chop2, it expresses a LACC protein.

The LACC of the present invention may also cause the modulation of the flow of anions such as chloride across a membrane when activated by light. Optically induced electrical and chemical changes due to activation of the LACC by light are also included within the invention.

In some embodiments of the invention it is desirable to add cofactor (usually in the nanomolar to micromolar range). In other embodiments, no addition of retinal is required. In some cases, the medium may provide the required cofactor. In a preferred embodiment of the present invention, the LACC protein covalently binds retinal. The term retinal, as used in comprises all-trans retinal, 11-cis retinal, and other isomers of retinal.

In some embodiments of the invention the protein Bcdo can be expressed along with ChR2. Bcdo converts the common dietary molecule beta carotene into retinal (Yan et. al., Genomics 72 (2):193 (2001)), thus providing retinal to convert Chop2 to ChR2.

As used herein, the terms "ChR2" and "Chop2" mean the full proteins or fragments thereof. A preferred embodiment of the present invention comprises the amino terminal 310 amino acids of Chop2 which is referred to herein as Chop2-310. A preferred embodiment the present invention comprises the amino terminal 310 amino acids of ChR2 which is referred to as ChR2-310. The amino-terminal 310 amino acids of ChR2 show homology to the 7-transmembrane structure of many microbial-type rhodopsins, and comprise a channel with a light-gated conductance. In an embodiment of the invention, a LACC protein comprises a 7-transmembrane protein. Preferably the LACC protein is a 7-transmembrane protein that either has a binding affinity for retinal, or has retinal bound to it.

In a preferred embodiment, the LACC of the present invention is derived from a microbial-type rhodopsin. In a preferred embodiment, the LACC of the present invention is derived from a bacteriorhodopsin.

One aspect of the present invention is a single-component protein that is a LACC protein. As used herein, a single component protein is a single covalently linked chain of amino acids. Multiple component systems require communication between non-covalently linked molecules, which can be much slower than within-protein signaling via conformational changes. Unlike previous methods requiring several protein components, the present invention allows the creation of light gated membrane conductance with a single protein component. While not being bound by theory, it is believed that the retinal in ChR2, as a microbial type rhodopsin, is strongly bound, allowing the retinal to re-isomerize to the all-trans ground state in a dark reaction without the need for other enzymes. This mechanism allows for fast recovery (closing of the ionic channel) when the light is removed, and it obviates the need for other enzyme components for re-generation of the all trans-retinal and closing of the channel.

In a preferred embodiment of the invention the light-activated cation-channel Channelrhodopsin-2 (ChR2) is genetically introduced into a cellular membrane.

The LACC protein of the present invention also comprises the protein sequence of Chop2-310 [SEQ ID NO:1, depicted in FIG. 12]. "Protein" in this sense includes proteins, polypeptides, and peptides. Also included within the LACC protein of the present invention are amino acid variants of the naturally occurring sequences, as determined herein. Preferably, the variants are greater than about 75% homologous to the protein sequence of Chop2 or Chop2-310, more preferably greater than about 80%, even more preferably greater than about 85% and most preferably greater than 90%. In some embodiments the homology will be as high as about 93 to about 95 or about 98%. Homology in this context means sequence similarity or identity, with identity being preferred. This homology will be determined using standard techniques known in the art. The compositions of the present invention include the protein and nucleic acid sequences provided herein including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

LACC proteins of the present invention may be shorter or longer than the protein sequence of Chop2 or Chop2-310. Thus, in a preferred embodiment, included within the definition of LACC proteins are portions or fragments of the protein sequence of Chop2 or of Chop2-310. In addition, nucleic acids of the invention may be used to obtain additional coding regions, and thus additional protein sequence, using techniques known in the art.

In a preferred embodiment, the LACC proteins of the present invention are derivative or variant protein sequences, as compared to Chop2 or Chop2-310. That is, the derivative LACC proteins of the present invention will contain at least one amino acid substitution, deletion or insertion, with amino acid substitutions being particularly preferred. The amino acid substitution, insertion or deletion may occur at any residue within the LACC protein.

Also included in an embodiment of the LACC proteins of the present invention are amino acid sequence variants of the ChR2, Chop2, ChR2-310, Chop-310 or [SEQ ID NO:1, depicted in FIG. 12]. These variants fall into one or more of three classes: substitutional, insertional or deletional variants. These variants ordinarily are prepared by site specific mutagenesis of nucleotides in the DNA encoding the LACC proteins, using cassette or PCR mutagenesis or other techniques well known in the art, to produce DNA encoding the variant, and thereafter expressing the DNA in recombinant cell culture. Amino acid sequence variants are characterized by the predetermined nature of the variation, a feature that sets them apart from naturally occurring allelic or interspecies variation of the LACC proteins of the present invention. The variants typically exhibit the same qualitative biological activity as the naturally occurring analogue, although variants can also be selected which have modified characteristics.

While the site or region for introducing an amino acid sequence variation is predetermined, the mutation per se need not be predetermined. For example, in order to optimize the performance of a mutation at a given site, random mutagenesis may be conducted at the target codon or region and the expressed breast cancer variants screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. In some embodiments, small alterations in the characteristics of the LACC proteins of the present invention are desired, substitutions are generally made in accordance with the following table:

TABLE I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile, | Leu, Val |
| Leu | Ile, Val |
| Lys | Arg, Gln, Glu |

TABLE I-continued

| Original Residue | Exemplary Substitutions |
|---|---|
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in Table 1. For example, substitutions may be made which more significantly affect the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants or derivatives typically exhibit the same qualitative activity as the Chop2, ChR2, Chop-310, or ChR2-310 protein, although variants or derivatives also are selected to modify the characteristics of the LACC proteins as needed. Variants or derivatives can show enhanced ion selectivity, stability, speed, compatibility, and reduced toxicity. For example, the protein can be modified such that it can be driven by different wavelength of light than the wavelength of around 460 nm of the wild type ChR2 protein. The protein can be modified, for example, such that it can be driven at a higher wavelength such as about 480 nm, 490 nm, 500 nm, 510 nm, 520 nm, 530 nm, 540 nm, 550 nm, 560 nm, 570 nm, 580 nm, or 590 nm.

The LACC proteins of the present invention can incorporate un-natural amino acids as well as natural amino acids. The unnatural amino acids can be used to enhance ion selectivity, stability, speed, compatibility, or to lower toxicity.

An aspect of the present invention is a fusion protein comprising a light-activated cation channel protein. It is well known in the art that fusion proteins can be made that will create a single protein with the combined activities of several proteins. In one embodiment, the fusion proteins can be used to target Chop2 or ChR2 to specific cells or regions within cells.

One embodiment of a fusion protein comprising a LACC protein is a fusion protein that targets sub-cellular regions of the cell. The fusion proteins can target, for instance, axons, dendrites, and synapses of neurons. In one preferred embodiment, a PDZ (PSD-95, Dlg and ZO-1) domain is fused to ChR2 or Chop2 which target dendrites. In another preferred embodiment, Axon initial segment (AIS) domain is fused to ChR2 or Chop2 which target axons.

Other fusion proteins of the present invention are proteins combining ChR2 and a fluorescent protein in order to allow for monitoring of the localization of ChR2. Preferred fusion proteins are those with red fluorescent protein (mCherry), yellow fluorescent protein (YFP), cyan fluorescent protein (CFP) and green fluorescent protein (GFP). These fusion proteins, such as the ChR2-mCherrry fusion protein, allow for the independent stimulation of ChR2 and the simultaneous monitoring of localization. The simultaneous stimulation and monitoring of localization can be carried out in many cell types including mammalian systems.

It is an aspect of the invention to provide a light-activated cation channel protein that is non-toxic in the cells in which it is expressed. Preferably, the light-activated ion channel proteins of the present invention do not perturb the basal electrical properties, alter the dynamic electrical properties, or jeopardize the prospects for cellular survival. Preferably, the light-activated cation channel proteins of the present invention do not alter the membrane resistance of the cells in the absence of light. Preferably, the light-activated ion channels do not lead to apoptosis in the cells, nor lead to the generation of pyknotic nuclei. Preferably, in the absence of light, the presence of the LACC protein does not alter cell health or ongoing electrical activity, at the level of subthreshold changes in voltage or in spike output, either by shunting current through leaky channels or by altering the voltage dependence of existing neuronal input-output relationships. Preferably, the presence of LACC protein creates no significant long-term plastic or homeostatic alterations in the electrical properties of neurons expressing the protein.

Another aspect of the present invention provides nucleic acid sequences which code for the LACC proteins of the present invention. It would be understood by a person of skill in the art that the LACC proteins of the present invention can be coded for by various nucleic acids. Each amino acid in the protein is represented by one or more sets of 3 nucleic acids (codons). Since many amino acids are represented by more than one codon, there is not a unique nucleic acid sequence that codes for a given protein. It is well understood by persons of skill in the art how to make a nucleic acid that can code for the LACC proteins of the present invention by knowing the amino acid sequence of the protein. A nucleic acid sequence that codes for a polypeptide or protein is the "gene" of that polypeptide or protein. A gene can be RNA, DNA, or other nucleic acid than will code for the polypeptide or protein.

One preferred embodiment of a nucleic acid sequence comprises [SEQ ID NO:2, depicted in FIG. 13].

It is known by persons of skill in the art that the codon systems in different organisms can be slightly different, and that therefore where the expression of a given protein from a given organism is desired, the nucleic acid sequence can be modified for expression within that organism.

An aspect of the present invention provides a nucleic acid sequence that codes for a light-activated cation protein that is optimized for expression with a mammalian cell. A preferred embodiment comprises a nucleic acid sequence optimized for expression in a human cell.

A preferred embodiment of a nucleic acid sequence that codes for a light-activated cation protein that is optimized for expression with a human cell comprises [SEQ ID NO:3, depicted in FIG. 14].

Another aspect of the present invention provides for reagents for genetically targeted expression of the LACC proteins including ChR2. Genetic targeting can be used to deliver light-activated cation channel proteins to specific cell types, to specific cell subtypes, to specific spatial regions within an organism, and to sub-cellular regions within a cell. Genetic targeting also relates to the control of the amount of light-activated cation channel protein expressed, and the timing of the expression.

A preferred embodiment of a reagent for genetically targeted expression of the LACC protein comprises a vector which contains the gene for the LACC protein.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of preferred vector is an episome, i.e., a nucleic acid molecule capable of extra-chromosomal replication. Preferred vectors are those capable of autonomous replication and/or expression of nucleic acids to which they are linked. Vectors capable of directing the expression of genes to which they are operatively linked are referred to herein as "expression vectors". Other preferred vectors are viruses such as lentiviruses, retroviruses, adenoviruses and phages. Preferred vectors can genetically insert LACC proteins into both dividing and non-dividing cells. Preferred vectors can genetically insert LACC proteins in-vivo or in-vitro.

Those vectors that include a prokaryotic replicon can also include a prokaryotic promoter capable of directing the expression (transcription and translation) of the LACC protein in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment of the present invention. Typical of such vector plasmids are pUC8, pUC9, pBR322, and pBR329 available from BioRad Laboratories, (Richmond, Calif.) and pPL and pKK223 available from Pharmacia, (Piscataway, N.J.).

Expression vectors compatible with eukaryotic cells, can also be used. Eukaryotic cell expression vectors are well known in the art and are available from several commercial sources. Typically, such vectors are provided containing convenient restriction sites for insertion of the desired DNA homologue. Typical of such vectors are pKSV-10 (Pharmacia), pBPV-1/PML2d (International Biotechnologies, Inc.), and pTDT1 (ATCC, No. 31255).

One preferred embodiment of an expression vector of the present invention is a lentivirus comprising the gene for ChR2 or Chop2 and an EF1-alpha promoter. This lentivirus vector is used in one aspect of the present invention to create stable cell lines. The term "cell line" as used herein is an established cell culture that will continue to proliferate given the appropriate medium.

One preferred embodiment of an expression vector of the present invention is a lentivirus comprising the gene for ChR2 or Chop2 and a cell specific promoter. Examples of cell specific promoters are promoters for somatostatin, parvalbumin, GABAα6, L7, and calbindin. Other cell specific promoters are promoters for kinases such as PKC, PICA, and CaMKII; promoters for other ligand receptors such as NMDAR1, NMDAR2B, GluR2; promoters for ion channels including calcium channels, potassium channels, chloride channels, and sodium channels; and promoters for other markers that label classical mature and dividing cell types, such as calretinin, nestin, and beta3-tubulin.

Another preferred embodiment is a lentivirus containing tetracycline elements that allow control of the gene expression levels of ChR2, simply by altering levels of exogenous drugs such as doxycycline. This method, or other methods that place ChR2 under the control of a drug-dependent promoter, will enable control of the dosage of ChR2 in cells, allowing a given amount of light to have different effects on electrical activation, substance release, or cellular development One aspect of the invention is nucleic acid sequences comprising the gene for LACC proteins and promoters for genetically targeted expression of the proteins. The genetically targeted expression of the LACCs of the present invention can be facilitated by the selection of promoters. The term "promoter" as used herein is nucleic acid sequence that enables a specific gene to be transcribed. The promoter usually resides near a region of DNA to be transcribed. The promoter is usually recognized by an RNA polymerase, which, under the control of the promoter, creates RNA, which is then converted into the protein for which it codes. By use of the appropriate promoter, the level of expression of LACC protein can be controlled. Cells use promoters to control where, when, and how much of a specific protein is expressed. Therefore, by selecting a promoter that is selectively expressed predominantly within one type of cell, one subtype of cells, a given spatial region within an organism, or sub-cellular region within a cell, the control of expression of LACC can be controlled accordingly. The use of promoters also allows the control of the amount of LACC expressed, and the timing of the expression. The promoters can be prokaryotic or eukaryotic promoters.

One embodiment of the invention is a nucleic acid sequence comprising the gene for LACC protein and a general purpose promoter. A general purpose promoter allows expression of the LACC protein in a wide variety of cell types. One example of a general purpose promoter of the present invention is The EF1-alpha promoter. The EF-1 alpha gene encodes for elongation factor-1 alpha which is one of the most abundant proteins in eukaryotic cells and is expressed in almost all kinds of mammalian cells. The promoter of this "housekeeping" gene can lead to persistent expression of the transgene in vivo. Another preferred general promoter is the CMV (cytomegalovirus) promoter, which can drive gene expression at very high levels. Still other preferred general-purpose promoters include those for CaMKII and synapsin I (Dittgen et. al, PNAS 101:18206-11 (2004)).

One embodiment of the present invention is a nucleic acid sequence comprising the gene for LACC protein and a cell specific promoter. Examples of cell specific promoters are promoters for somatostatin, parvalbumin, GABAα6, L7, and calbindin. Other cell specific promoters are promoters for kinases such as PKC, PKA, and CaMKII; promoters for other ligand receptors such as NMDAR1, NMDAR2B, GluR2; promoters for ion channels including calcium channels, potassium channels, chloride channels, and sodium channels; and promoters for other markers that label classical mature and dividing cell types, such as calretinin, nestin, and beta3-tubulin. In a preferred embodiment of the present invention, the nucleic acid comprises a bacterial artificial chromosome (BAC).

One embodiment of the present invention is promoter is an inducible promoter. For instance, the promoter can be inducible by a trans-acting factor which responds to an exogenously administered drug. The promoters could be, but are not limited to tetracycline-on or tetracycline-off, or tamoxifen-inducible Cre-ER.

Cells

One aspect of the present invention is a cell that expresses LACC proteins, and specifically a cell that expresses ChR2 or Chop2. Another aspect of the invention is a LACC protein expressing-cell that also expresses other ion channels, receptors, or signaling proteins, both in the normal and/or impaired form. Another aspect to the invention is a business method to make commercially available the cells of the invention.

The cells of the present invention can be created using a vector including a DNA expression vector, a virus or an organism. Preferred vectors include lentiviruses and retroviruses. In some cases, in particular where robust cell lines are involved, expression of ChR2 can be induced by using lipofection techniques, such as exposing cell lines to micelles containing Lipofectamine or Fugene, and then FACS-sorting to isolate stably expressing cell lines.

Cells of any origin, preferably those cells that are capable of growth in tissue culture, are candidate cells for transfection or infection with a LACC protein such as ChR2 or Chop2. Non-limiting examples of specific cell types that can be grown in culture include connective tissue elements such as fibroblast, skeletal tissue (bone and cartilage), skeletal, cardiac and smooth muscle, epithelial tissues (e.g. liver, lung, breast, skin, bladder and kidney), neural cells (glia and neurones), endocrine cells (adrenal, pituitary, pancreatic islet cells), bone marrow cells, melanocytes, and many different types of hematopoetic cells. Suitable cells can also be cells representative of a specific body tissue from a subject. The types of body tissues include, but are not limited to, blood, muscle, nerve, brain, heart, lung, liver, pancreas, spleen, thymus, esophagus, stomach, intestine, kidney, testis, ovary, hair, skin, bone, breast, uterus, bladder, spinal cord and various kinds of body fluids. Cells in culture can be freshly isolated from body tissues (known as primary culture) or subcultured by expansion and/or cloning of the cells present in the primary culture (known as cell lines).

Cells of different developmental stages (embryonic or adult) of an organism, or more specifically of various developmental origins including ectoderm, endoderm and mesoderm, can also be applied. Another type of cells embodied in the present invention is a "personal cell type", which comprises cells derived from individuals of a family, or individuals from different generations within the same pedigree.

Of particular interest are cells that are associated with a particular disease or with a specific disease stage, cells derived from natural and induced immune deficiency states, cardiovascular disease, neuronal disease, inflammation states and diseases caused by a variety of pathogens. The association with a particular disease or disease stage may be established by the cell's aberrant behavior in one or more biological processes such as cell cycle regulation, cell differentiation, apoptosis, chemotaxis, cell motility and cytoskeletal rearrangement. A disease cell may also be confirmed by the presence of a pathogen causing the disease of concern (e.g. HIV for AIDS and HBV for hepatitis B).

Preferred cells are mammalian cells and cell lines derived from mammalian cells. Other preferred cells are embryonic stem cells and adult stem cells including hematopoietic stem cells, bone marrow, neural stem cells, epithelial stem cells, skin stem cells. Preferred cell lines appropriate for ChR2 expression include, HEK cells, neural stem cell lines, pancreatic islet cell lines, and other excitable or secretory cells.

The LACC proteins, when activated by light can also cause other ion channel proteins within the membrane to be activated. Thus, an aspect of the invention is a cell that has both the LACC protein and other ion channels or a splice variant of an ion channel that can be activated by the LACC protein. Examples of ion channels include, but are not limited to, Voltage-gated channels such as sodium and potassium voltage-gated channels of nerve and muscle; Ligand-gated such as Acetylcholine receptor, AMPA receptor and other neurotransmitter-gated channels; Cyclic nucleotide-gated channels such as calcium-activated channels; cardiac ion channels such as HERG channels; Stretch-activated channels; G-protein-gated channels; Inward-rectifier K channels; Resting channels; Store-operated channels such as calcium release-activated calcium (CRAC) channel; as well as other calcium channels, other potassium and sodium channels. The one or more ion channel proteins can be artificial, and can be targeted to be expressed in the cell containing the LACC protein.

A preferred embodiment of the invention is a cell that comprises a LACC protein and one or more ion channel proteins that can be activated and thus controlled and whose behavior can be understood. Another preferred embodiment of the invention is a cell that comprises a LACC protein and one or more ion channel proteins that can be activated and thus controlled for screening for ion channel modulators as described below. Another preferred embodiment of the invention is a cell that comprises a LACC protein and one or more cardiac ion channels (e.g. HERG channel) that can be activated and thus controlled for screening for side effect of compounds as described below. Another preferred embodiment is an article of manufacture as described below containing a cell that comprises a LACC protein and one or more ion channel proteins that can be activated as described by the method herein.

A preferred cell that expresses LACC proteins, and specifically a cell that expresses ChR2 or Chop2 is a mammalian cell.

One aspect of the present invention is a cell line that expresses LACC proteins, and specifically a cell line that expresses ChR2 or Chop2. The cell line of the present invention can be created using a vector including a DNA expression vector, a virus or an organism. Preferred vectors include lentiviruses and retroviruses. In some cases, in particular where robust cell lines are involved, expression of ChR2 can be induced by using lipofection techniques, such as exposing cell lines to micelles containing Lipofectamine or Fugene, and then FACS-sorting to isolate stably expressing cell lines. Preferred cell lines are mammalian cell lines as described above. Preferred cell lines are neuronal cell lines or other excitable cell lines. Preferred cell lines appropriate for ChR2 expression include HEK cells, neural stem cell lines, pancreatic islet cell lines, and other excitable or secretory cells.

A preferred cell line of the present invention is a clonal neuronal stem cell line expressing ChR2 under the EF1-alpha promoter. Such a cell line is useful for the screening of drugs, particularly drugs that affect the influence of electrical activity on neuronal genesis, development, and apoptosis.

Another preferred cell line of the present invention is a line of hippocampal neurons that expresses ChR2 under the EF1-alpha promoter. Such a cell line is useful for the in-vitro screening of drugs, and as a model for controlling neurons with light in-vivo.

An embodiment of the invention is a stem cell lines that provide therapies based on transplantable, optically activatable cells that release substances as described below such as insulin, growth hormones, or other small molecules or polypeptides. Control of substance release with the present invention can be done on the second-to-minute timescale, allowing precise management of drug dosing, especially for conditions like diabetes or growth retardation.

The cells of the invention can be grown as a monolayer anchored onto a solid phase substrate, or as aggregates in a suspension culture. The choice of substrate is determined largely by the type of cell and the desired growth parameters (e.g. growth rate, desired density, media requirements etc.) Most cells can be propagated on a substrate made of e.g., glass, plastic or ceramic material. For certain cell types, such as neurons, epithelial and muscle cells, substrates pre-coated with charged substances that enhance cell attachment and spreading are preferred. Commonly employed coating materials include biological substrates that bear a net positive charge. Non-limiting examples of biological substrates include extracellular matrix/adhesion proteins such as laminin, fibronectin, collagen, or synthetic polypeptide such as poly-lysine. A variety of non-biological substrates such as membranes made of nitrocellulose, nylon, polytetrafluoroethylene, or any other implant materials can also be used to support growth of cells in a suitable medium according to cell type.

Precautions are generally taken to maintain membrane integrity and preserve cell membrane components when harvesting cells cultured on different substrates. The method of the invention contemplate the use of traditional method of dissociating of anchored cells or cell layers including proteolytic enzymes such as serine proteinase, trypsin. In addition cells of the present invention can be removed from the culture substrates by agents that minimize damages to the cell surface antigens. These agents include chelating agents, such as EDTA and EGTA, which bind to divalent metal ions (e.g. calcium and magnesium) known to be necessary for cell-substrate attachment. Other suitable cell dissociation agents encompass collagenases, dispases, and neutral proteinases when used in conjunction with serine proteinase inhibitors (e.g. soybean trypsin inhibitor). Treatment of cells with these agents mostly results in disruption of the extracellular matrix components while preserving the cell surface proteins. The time required to detach the cells anchored on a solid substrate can vary depending on the protease enzymes chosen, but will normally be a period of about 1 minute to 30 minutes, and preferably about 5 minutes to 15 minutes. The enzymatic treatment can be carried out at room temperature or at about 37° C. Excess enzyme can be removed by gentle washing with buffers having pH and salt concentrations in the physiological range that are routinely prepared by one skilled in the art.

Cell viability may be confirmed by the measurement of membrane integrity. The methods for assessing membrane integrity are known in the art. The most common assay involves staining cells with a dye that reacts with either living or dead cells. As is apparent to one skilled in the art, exemplary dyes include trypan blue, eosin Y, naphthalene black, nigrosin, erythrosin B and fast green.

Transgenic Animals

One aspect of the invention is a transgenic animal that expresses a LACC protein. A preferred embodiment is a transgenic animal that expresses Chop2 or ChR2. Expression of LACC protein in particular subsets of neurons can be used for analyzing circuit function, behavior, plasticity, and animal models of psychiatric disease Preferred transgenic animal species of the present invention that expresses LACC protein include zebrafish (*Danio rerio*). In zebrafish, the LACC protein can be introduced fish embryos by acute injection at the few-hundred cell stage.

Another preferred transgenic animal species of the present invention that expresses LACC protein is flies (*Drosophila melanogaster*). In one preferred embodiment, flies express ChR2 under the UAS promoter for use in the GAL4-UAS system). Another preferred transgenic animal species of the present invention that expresses LACC protein is worms (*Caenorhabditis elegans*). In one preferred embodiment, stable lines are made with injection of plasmids containing ChR2 under specific promoters into the gonad.

Another preferred transgenic animal species of the present invention that expresses LACC protein is mice. In one preferred embodiment, mice that express LACC protein are made using BAC (bacterial artificial chromosome) transgenic technology, as well as position effect variegation techniques.

One preferred embodiment of a transgenic animal of the present invention that expresses LACC protein is *Drosophila* in which ChR2 is expressed in serotonergic and dopaminergic neurons, which are important for the driving of motivated behavior and the creation of finely tuned motor patterns.

One preferred embodiment of a transgenic animal of the present invention that expresses LACC protein is *Caenorhabditis elegans* in which ChR2 is expressed in serotonergic and dopaminergic neurons, which are important for the driving of motivated behavior and the creation of finely tuned motor patterns.

Another preferred embodiment of the present invention is a transgenic animal wherein the LACC is expressed under a specific promoter. Another preferred embodiment of the present invention is a transgenic animal wherein the LACC expressed in the transgenic animal is introduced via a BAC. Another preferred embodiment of the present invention is a transgenic animal wherein the LACC gene is knocked into a known locus.

Channel Properties

In the present invention, electrical spikes, or action potentials, are created across a membrane by illumination with light. The light can be provided by a light source such as a xenon lamp, or the light source can be a laser. While a laser can be used, it would be understood by one skilled in the art that if the intensity of light is too high, there can be damaged to the cells under illumination due to local heating, etc. It is preferred to use a light intensity that does not damage the cells. In a preferred embodiment of the present invention medium intensity light is used to activate the ion channel. A preferred level of light is between about 0.1 mW/mm2 and about 500 mW/mm2, preferably from about 1 mW/mm2 and about 100 mW/mm2, and most preferably from about 5 mW/mm2 and about 50 mW/mm2. In a preferred embodiment, the LACC protein is ChR2 and the wavelength of the illuminating light is between about 400 nm and about 600 nm, preferably from about 450 nm and about 550 nm, most preferably from about 450 nm and about 490 nm.

In accordance with the present invention, it has been discovered that the light-activated ion channels of the invention can generate millisecond-timescale spikes when incorporated into neurons and illuminated with rapid pulses of light.

One aspect of the present invention is a light-activated ion channel that is expressed in an excitable cell and will operate on the millisecond timeframe. In a preferred embodiment, a LACC responds within 100 millisecond (ms), more preferably within 10 ms, even more preferably within 1 ms, and most preferably within 0.1 ms. A preferred embodiment of the present invention is ChR2 that is expressed in a neuron or other excitable cell.

In accordance with this invention, it has also been discovered that a cell expressing a LACC of the present invention will reliably generate spikes on the millisecond timeframe.

In a preferred embodiment of a light-activated ion channel that is expressed in an excitable cell and will operate on the millisecond timeframe, the excitable cell responds in less than 10 ms, preferably less than 5 ms, and most preferably within 1 ms of being illuminated.

One aspect of the present invention is a LACC protein expressed in a cell membrane that provides stable photocurrents over long time scales. In a preferred embodiment the LACC protein is ChR2, and the photocurrent does not change by more than 20% over an hour of illumination, preferably not more than 10%, and most preferably not a detectable change over an hour of illumination.

One aspect of the present invention is a LACC protein expressed in a cell membrane that provides precisely timed spikes with low temporal jitter. The temporal jitter is preferably lower than 10 ms, more preferably less than 5 ms, and most preferably lower than 3 ms when measured within neurons.

One aspect of the present invention is a LACC protein expressed in a cell membrane that provides low temporal jitter across neutrons. Low temporal jitter across neutrons is desirable because it allows heterogeneous populations of neutrons to be controlled in concert. Preferably the temporal jitter across neutrons is also less than 10 ms, more preferably less than 5 ms, and most preferably lower than 3 ms. Preferably the across neutron jitter is within 50% of the within neutron jitter, most preferably the across neutron jitter is within 20% of the within neutron jitter, most preferably the within neutron jitter is indistinguishable from the across neutron jitter.

One aspect of the present invention is a LACC protein expressed in a membrane that provides reliable and precisely timed subthreshold pulses.

It has been discovered that a cell expressing a light-activated cation channel protein of the present invention showed small trial-to-trial variability in the subthreshold deflections evoked by repeated light pulses. The light-activated cation channel proteins of the present invention such as ChR2 can therefore be employed to drive reliably timed subthreshold depolarizations with precisely determined amplitude.

An aspect of the present invention is a LACC protein expressed in a membrane that has repeatable subthreshold polarizations. In a preferred embodiment of the invention, the LACC protein expressed in a membrane generates subthreshold pulses with a coefficient of variation of less than 0.2 when measured over 5 consecutive pulses, more preferably the coefficient of variation is less than 0.15 when measured over 5 consecutive pulses, and most preferably the coefficient of variation is less than 0.10 when measured over 5 pulses.

The present invention allows for the optical control of cell properties by expressing a LACC protein within the cell, and activating the protein with light. The invention allows the optical control of excitable cells. One type of control is the control of electrical properties of the cell membrane for processes such as control of neurons and of transmissions of signals between neurons. Another type of control is control of influx of ions including Ca+2. The control of influx of Ca+2 is known to affect thousands of cellular processes. The optical control of the properties of excitable cells can be carried out in-vivo or in-vitro, and can be used for understanding biological processes, for drug discovery, and for therapeutic uses.

Another type of control provided by the present invention is the use of the activation of the LACC protein to cause the cell to release proteins, peptides, or small molecules. In one embodiment of the invention, through the light activation of LACC protein, the cell can be caused to release a protein, such as a cytokine. In one embodiment of the invention, through the light activation of ChR2, the cell can be caused to release a peptide such as insulin, leptin, neuropeptide Y, substance P, human growth hormone, secretin, glucagon, endorphin, oxytocin, vasopressin, or orexin/hypocretin. In another embodiment, the activation of the LACC protein can cause the release of a small molecule whose synthesis or release is dependent on electrical activity, such as nitric oxide, or a cannabinoid such as anandamide or 2-arachidonylglycerol (2-AG).

The present invention also allows for the control of cellular activity beyond the release of substances. For instance, LACC expressed in a muscle cell can allow for optical control of muscle cell contraction. This optical contraction of muscle cells, especially the contraction of specific muscle cells in the presence of other muscle cells, can be used for therapeutic purposes, or for the optical control of muscular contractions.

The control provided by the present invention also included initiating specific intracellular signal conduction pathways. These pathways include, but are not limited to, kinases, transcription factors, and second messenger systems. These pathways can be specifically activated by the present invention due to the specific temporal pattern of light that is used. The pathways can also be specifically activated due to the specific sub-cellular localization of the LACC.

An aspect of the present invention is a method of optically controlling a cell comprising; causing the cell to express LACC protein; and illuminating the cell with light to activate the LACC protein.

A preferred embodiment of the method of optically controlling cell properties is a method in which the LACC protein is ChR2.

Another preferred embodiment of the method of optically controlling cell properties is a method in which the cells are neurons or other excitable cells. The neurons can be connected to other neural cells and can be in a neural network.

Another preferred embodiment of the method of optically controlling cell properties is a method in which the cells are spatially or genetically targeted subsets of cells that express the LACC protein of the present invention and can be specifically activated.

Another preferred embodiment of a method of controlling cell properties comprises a method wherein the activation of the LACC also controls other ion channels within the cell. For instance, a cell can be caused to express LACC and one or more other ion channel proteins which may be artificial proteins. The LACC activation can then be used to activate or inactivate the other ion channel proteins within the cell. In one embodiment, a cell expressing LACC can be illuminated with light in order to depolarize the cell membrane sufficiently to inactivate the cell's other ion channels.

One aspect of the invention is a method of driving cell differentiation using light. LACC protein can be used to selectively target differentiating cells whose cell fate is dependent on activity. For example, ChR2 can be delivered to a progenitor cell or cell line, and then light can be used to drive the differentiation of the cell into appropriate progeny.

In accordance with this invention, it has also been discovered that a cell expressing a light-activated cation channel protein of the present invention will reliably generate spikes on the millisecond timeframe if the optical illuminations is provided in pulses in which a rapid light pulse is followed by a period of darkness.

In a preferred embodiment of the method of optically controlling cell properties is a method comprising illuminating the cell with the LACC protein with a series of light pulses in which light periods are from 0.1 ms to 100 ms), preferably from 1 ms to 50 ms, most preferably between 5 ms and 20 ms, and the periods of darkness were greater than 1 ms, preferably greater than 10 ms, and most preferably greater than 20 ms. The periods of darkness can be long if desired, and can be periods of greater than seconds to minutes.

The methods of optically controlling cell properties of the present invention will result in the ability to probe causal function in intact neural circuits, with it becoming possible to examine the role of particular neurons in animal models of learning, emotion, motor coordination, and sensory processing. This will enable the discovery of drugs capable of modulating whole-circuit function, essential for the addressing of complex neurological and psychiatric diseases. For the first time, genetically-targeted neurons within animals will be addressable by light on timescales appropriate for examining the neural code mediating the behavioral or circuit-dynamics function observed, whether normal or dysfunctional.

The millisecond scale control of electrical signals in neurons that is made possible by the present invention creates the ability to control synaptic events. The ease of eliciting synaptic transmission allows LACC proteins of the present invention including ChR2 to be an ideal tool for the temporally precise analysis of neural circuits.

Another aspect of the present invention is the use of light to create a synaptic event. A LACC protein of the present invention expressed within a neuron can be activated by light to create an electrical signal within the neuron. That electrical signal can propagate along the neuron to the synapse where the signal can elicit a synaptic event. The synaptic event can be either an electrical or a chemical synaptic event. In a preferred embodiment the synaptic event releases a small molecule that can modulate cellular function. In a preferred embodiment, the synaptic event comprises the release of a small-molecule neuromodulator such as norepinephrine, serotonin, dopamine, acetylcholine, D-serine, or histamine. The synaptic event can result in a synaptic transmission between two neurons. The present invention thus provides optically driven communication between sets of neurons, and thereby provides optically driven activity throughout a connected neural network.

A preferred embodiment for the use of light to create a synaptic event comprises expressing ChR2 in a first neuron and illuminating the neuron with pulse of light to activate ChR2 to create a spike which causes a synaptic event. The use of light to create synaptic events can be carried out in-vitro or in-vivo.

Another preferred embodiment for the use of light to create a synaptic event comprises expressing ChR2 in a first neuron and that in synaptic contact with a second neuron, and illuminating the first neuron so as to create a spike, wherein the spike results in a synaptic event at the synapse between the first and second neurons, and the second neuron is either excited or inhibited due to the signal from the first neuron, thus resulting in a synaptic transmission between the first and second neurons.

Another preferred embodiment for the use of light to create a synaptic event comprises using a vector that is targeted to deliver the LACC protein of the present invention to specific neurons, specific subsets of neurons, or specific neuronal subtypes. The targeted delivery can be a specific spatial targeting into different spatial areas of the specimen, and/or the targeted delivery can be to chemical targeting to molecularly defined classes or subclasses of neurons.

Targeted Delivery of LACC

An aspect of the invention is a method for targeted delivery of light-activated cation-channel proteins to specific cells comprising; contacting said cells with a vector comprising a nucleic acid sequence comprising a LACC protein and a cell specific promoter; wherein said specific cells express said LACC protein.

A preferred embodiment of a method for targeted delivery of light-activated cation-channel proteins to specific cells comprises a method wherein the vector comprises a nucleic acid sequence that codes for Chop2 or ChR2 and a cell specific promoter. Preferred cell specific promoters are the promoters for somatostatin, parvalbumin, GABAα6, L7, and calbindin. Other cell specific promoters are promoters for kinases such as PKC, PICA, and CaMKII; promoters for other ligand receptors such as NMDAR1, NMDAR2B, GluR2; promoters for ion channels including calcium channels, potassium channels, chloride channels, and sodium channels; and promoters for other markers that label classical mature and dividing cell types, such as calretinin, nestin, and beta3-tubulin.

A preferred embodiment of a method for targeted delivery of light-activated cation-channel proteins to specific cells comprises a method wherein the vector comprises a lentivirus or a retrovirus.

An aspect of the invention is a method for targeted delivery of light-activated cation-channel proteins to specific cells comprising; contacting said cells with a vector comprising a nucleic acid sequence comprising a LACC protein wherein said vector selectively targets specific cells. Preferred vectors are lentiviruses and retrovirus.

Methods of Treatment

Another aspect of the invention is a method for treating a subject comprising delivering a vector comprising a LACC protein to excitable cells within the subject and illuminating said cells with pulses of light.

A preferred embodiment of a method for treating a subject comprises performing human therapeutic functions in which the function of cells is rescued or controlled by the genetic addition of LACC proteins such as ChR2, accompanied by the use of physically delivered pulses of light, preferably blue light. Delivering a LACC protein such as ChR2 in human patients via viral vectors can enable control of excitable cells by blue light, either from a wearable optical device (for chronic stimulation) or at a fixed optical station (for more occasional stimulation). For example, peripheral neurons like cutaneous pain suppressing nerves, virally transduced to express ChR2, allow light stimulation to activate dorsal column-medial lemniscus neurons in order to suppress painful C fiber responses. It has been shown that modified herpes viruses can be used to deliver ion channels to pain-pathway neurons; which can be used herein with ChR2 for the targeting of the channel to pain-pathway neurons and for reduction of the perception of pain. Similarly, patients who have rod or cone loss (such as in retinitis pigmentosa or macular degeneration) can be virally transduced to express a LACC protein such as ChR2 in retinal ganglion cells, which restores the transduction of light in pathways mediating visual perception. For instance, it has been shown that long-term expression of a microbial-type rhodopsin, channelrhodopsin-2 (ChR2), can be achieved in rodent inner retinal neurons in vivo using delivery by an adeno-associated viral vector. It was demonstrated that expression of ChR2 in surviving inner retinal neurons of a mouse with photoreceptor degeneration can restore the ability of the retina to encode light signals and transmit the light signals to the visual cortex (Bi et al. *Neuron* 50, 23-33 (2006)). Thus, the strategy based on the expression of ChR2 is suitable for retinal degenerative diseases. In another example, ChR2-expressing T lymphocytes that attack cells bearing self-antigens can be induced to undergo apoptosis where illumination induces significant Ca+2 influx; this can be done ex vivo on blood that passes through an optical illumination device.

In one embodiment, the optical device used to excite LACC protein-expressing cells in patients is a light-emitting diode (LED). The LED can be in the millimeter or nanometer scale in size. One non-limiting example includes SML0805-B1K-TR LEDtronics. The LED can be battery-powered or remotely power by RF by methods that are known in the art. The LED can also be couple to a 68-microHenry surface-mount ferrite core inductor such as CF1008-682K from Gowana Electronics, NY. In one embodiment, the wearable optical device can be non-invasively activated in a non-wireless fashion.

The methods and compositions provided herein can provide a beneficial effect for depression patients. Preferably depression patients are treated by delivering and exciting a LACC protein such as ChR2 to the anterior and/or subgenual cingulate cortex and to anterior limb of internal capsule of human patients by the methods described herein.

The methods and compositions provided herein can also provide a beneficial effect for chronic pain patients. Preferably chronic pain patients are treated by delivering and exciting a LACC protein such as ChR2 to the anterior and/or dorsal cingulate cortex of human patients by the methods described herein.

Similarly, the methods and compositions provided herein can provide a beneficial effect for obesity patients. Preferably obesity patients are treated by delivering and exciting a LACC protein such as ChR2 to the ventromedial nucleus of the thalamus of human patients by the methods described herein.

Similarly, the methods and compositions provided herein can provide a beneficial effect for obsessive compulsive (OCD) patients. Preferably OCD patients are treated by delivering and exciting a LACC protein such as ChR2 to the anterior limb of internal capsule subthalamic nuclei of the thalamus of human patients by the methods described herein.

Similarly, the methods and compositions provided herein can provide a beneficial effect for addiction patients. Preferably addiction patients are treated by delivering and exciting a LACC protein such as ChR2 to the nucleus accumbens and septum of human patients by the methods described herein.

Similarly, the methods and compositions provided herein can provide a beneficial effect for Alzheimer's patients. Preferably Alzheimer's patients are treated by delivering and exciting a LACC protein such as ChR2 to hippocampus of human patients by the methods described herein.

Similarly, the methods and compositions provided herein can provide a beneficial effect for Parkinson's patients. Preferably Parkinson's patients are treated by delivering and exciting a LACC protein such as ChR2 to the subthalamic nuclei and/or globus pallidus of human patients by the methods described herein.

Another route for human therapy using a LACC protein such as ChR2 is to create a LACC protein-expressing secretory cell for implantation in patients (for example, nanoencapsulated to avoid immune responses) in which secretion is stimulated in the cells by the use of physically delivered pulses of light. For example, ChR2-expressing neuroendocrine cells that release thyroid hormones (such as T4, TRH, and others) can be implanted subcutaneously to allow for controlled peptide release over timescales from months to years. Sequences of flashes of light allow controlled release of such neuroendocrine substances, allowing modulation of stress, reproduction, metabolism, and sleep. Similarly, LACC protein-expressing pancreatic islet cells can be made to release insulin when stimulated with light; implanted cells can enable control of diabetes symptoms on a minute-to-minute timescale without need for pump implantation or other invasive therapy.

In one embodiment, LACC protein-expressing cells are encapsulated prior to implantation into patients. The cells can be macroencapsulated or nanoencapsulated. Examples of capsules include but are not limited to semipermeable membranes, hollow fibers, beads and planar diffusion devices. For example, encapsulation of dopamine-secreting cells in a semipermeable membrane has been examined to avoid rejection of implanted cells by the immune system (Emerich et al. *Neurosci Biobehav Rev* 16, 437-447). The selectively permeable nature of the polymer membrane permits bidirectional access of low molecular weight compounds, including the inward diffusion of glucose, oxygen and other vital nutrients, and the outward diffusion of dopamine. The membrane restricts the passage of elements of the host immune system, thereby preventing host rejection of the encapsulated cells. For example, it has been shown that encapsulated PC 12 cells, a catecholaminergic cell line derived from rat pheochromocytoma, can be implanted into the striatum of monkeys and adult guinea pigs (Date et al. *Cell Transplant* 9, 705-709, Aebischer et al. *Exp Neurol.* 111, 269-275). In addition, it has been shown that xenotransplantation of islets or insulin producing cells encapsulated within hollow fibers, macrobeads, or planar diffusion devices can reverse hyperglycemia in mice and rats (Tatarkiewicz et al. *Transplantation* 67(5) 665-671).

In another embodiment, LACC protein-expressing cells are generated in the capsule prior to transplantation. For instance, ES cells can be: i) differentiated into dopamine producing neurons, ii) transfected with a nucleic acid containing LACC as described above, and iii) grown in a capsule, prior to implantation into patients. It has been shown that dopaminergic neurons can be induced from ES cells from mouse enclosed in hollow fibers using conditioning medium from PA6 cells, the stromal cells derived from skull bone marrow (Yamazoe et al. *Biomaterials* 27 (2006) 4871-4880). In these studies β-tubulin type III positive cells and tyrosine hydroxylase positive cells were efficiently derived in hollow fibers after 16 days in culture, and dopamine release was observed when the hollow fibers containing cells were exposed to 56 mM KCl for 15 min to induce dopamine release through depolarization of the neurons.

In another embodiment, differentiated LACC protein-expressing stem cells capable of secreting dopamine would be implanted, directly into the brain of a patient, and then drive their activation using light. Dopamine-secreting cells can be transfected or infected as described herein with a LACC protein such as ChR2, before or after the differentiation step, and then these cells can be implanted into the brain of the patients. The LACC protein-expressing stem cells are then activated by an optical device such as a light-emitting diode or a laser with an optical fiber attached to the end. Since the cells are light responsive, they will release dopamine even deep within tissue, simply by remotely being stimulated with light.

Figure 10:
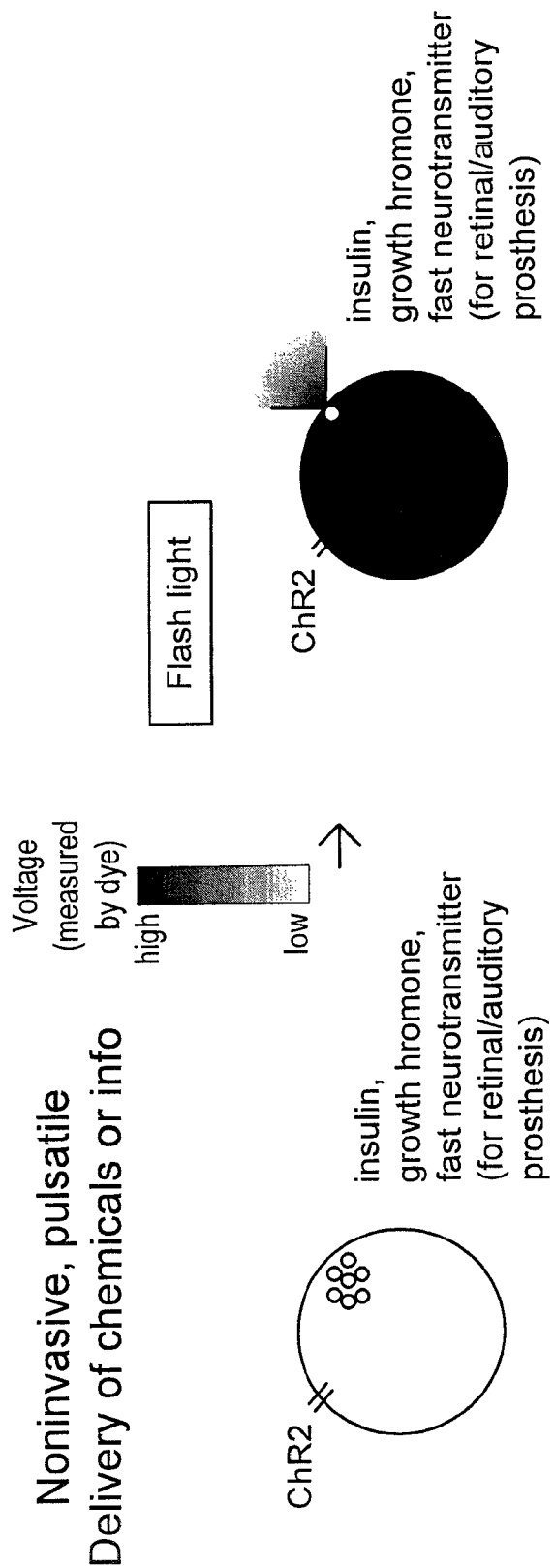
FIG. 10 illustrates an embodiment of one of the methods of the invention.

In another embodiment, LACC protein-expressing secretory cells are implanted into a tissue or an organ of a patient. The secretory cell is transfected or infected is described herein with a LACC protein such as ChR2, and then these cells are implanted into the tissue or organ of the patient. The LACC protein-expressing secretory cells are then induced to secrete chemicals by an optical device such as a light-emitting diode or a laser with an optical fiber attached to the end. FIG. 10 illustrates one embodiment of the methods described herein, wherein cells expressing ChR2 (by transfection or infection) allow release of substances to be controlled by pulses of light.

Examples of tissues or organs that can be implanted with LACC protein-expressing secretory cells include, but are not limited to epithelium, connective tissue, connective tissue, nervous tissue, heart, lungs, brain, eye, stomach, spleen, pancreas, kidneys, liver, intestines, skin, uterus, and bladder.

Examples of chemicals that can be secreted into the tissue or organ of a patient by the methods described herein include but are not limited to insulin, growth hormone, fast neurotransmitter, dopamine, cytokines, chemokines, hormones and hormone antagonists, pituitary hormones and their hypothalamic releasing factors, thyroid and antithyroid drugs, estrogens and progestins, androgens, adrenocorticotropic hormone; adrenocortical steroids and their synthetic analogs;

inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

In one embodiment, LACC protein-expressing secretory cells are implanted into the skin of a diabetic or patient. The LACC protein-expressing secretory cells are then induced to secrete insulin by an optical device such as a light-emitting diode or a laser with an optical fiber attached to the end.

A LACC protein such as ChR2 allows for temporal, non-invasive control of release of substances from excitable cells. It should be apparent that the electrical activity, Ca+2, and secretion of different chemicals can affect literally thousands of cellular processes. Thus, it is possible that the general arena of applications of a LACC protein such as ChR2 in vivo may enable control over many biological disease processes in a variety of systems.

Controlling Organism or Cells

Another aspect of the present invention is a method of controlling the behavior of an organism comprising delivering a vector comprising a LACC protein to excitable cells within the organism; and illuminating said cells with pulses of light so as to control the behavior of the organism.

Another aspect of the invention involves the use of the method described herein to control the fate of cells. The techniques described herein are used to modulate activities of cells that are modulated by electrical activity. The methods can be used to modulate the survival, replication, differentiation, and/or death of cells. Channelrhodopsin is used to drive any one of these processes, depending on the precise pattern of stimulation used to drive activation of channelrhodopsin, which would then result in a specific pattern of downstream signal transduction and a specific cellular fate response. Thus, targeting Channelrhodopsin to specific cells, then exposing them to particular light patterns is used to enhance the survival of, drive differentiation or replication of, or hasten the death of, the cells expressing the light-activated channel. This modulation of cellular processes is preferably used in stem cells, where particular patterns of activity may drive the differentiation of stem cells (including human embryonic stem cells), drive the replication of stem cells, or drive the death of the stem cells (in the case where excessive replication is desired to cease). If the target cells are tumor or cancer cells, then targeting channelrhodopsin to those cells permits the use of specific and appropriate patterns of light to kill the tumor/cancer cells. Other suitable target cells include various secretory or organ cells or their precursors, cardiac or other muscle cells, or glial cells in the brain. In each of these cases, it may be desirable to control the replication, differentiation, and death of these cells precisely. Channelrhodopsin may be useful for controlling these things in vitro, in vivo in experimental animals, or in vivo in humans (before or after transplantation into the body).

Drug Screening

An aspect of the invention is a method for screening for drugs comprising expressing a LACC protein in a group of cells; exposing said group of cells to a compound; illuminating said groups of cells with light; and monitoring the electrical response of cells within the group of cells. The electrical response of cells can be monitored electrically, optically, or by other means. The electrical responses of the cells can be seen and monitored using chemical or voltage-sensitive dyes, or dyes that undergo oxidation or reduction. These changes can be monitored in a microscope, with optical sensors or with a camera using film, CCD arrays, and other methods known by persons of skill in the art.

A preferred embodiment of a method of drug screening is high-throughput screening for drugs affecting the ionic and signaling function of cells such as central and peripheral neurons, heart muscle, pancreatic islet cells, neuroendocrine cells in pituitary and kidney, stem cells, cancer cells, and others.

A preferred embodiment of a method of drug screening comprises rapidly modulating voltage in electrically excitable cells capable of fast responses (such as neurons and heart muscle, or cell lines derived thereof), to screen for drugs that block or activate voltage-gated ion channels, alter excitatory or inhibitory synaptic transmission (play a role in epilepsy and pain), and alter muscular contraction. Since many channels and receptors activate rapidly, and then desensitize or inactivate, the ability to control membrane voltage with brief pulses of light greatly enhances the ability to develop drugs that target certain channel, synapse, or muscle disease phenotypes. For example, familial hemiplegic migraine patients have point mutations in a calcium channel, reducing the calcium influx, for a given brief depolarization. The methods of the present invention will allow for screening drugs that modulate the calcium response (measured using a calcium dye) to a given stereotyped depolarization, in a cell line expressing the mutant calcium channel and ChR2, to discover ways of improving channel function in this patient population.

There are many cells that do not always rapidly change voltage, but nevertheless have significant functions in the body downstream of electrically-driven Ca+2 influx. For example, pancreatic islet cells and neuroendocrine cells (e.g., those of the thyroid, pituitary, and adrenal glands) release hormones in a Ca+2-dependent way, via the fusion of dense core vesicles. LACC proteins of the present invention such as ChR2, which not only causes cell depolarization but is capable of passing Ca+2 ions through its channel pore, can be used to activate the release of peptides or hormones from such cells (or derived cell lines), aiding in the screening of drugs that enhance or suppress hormone release. Such discoveries can aid in the discovery of pharmacological methods of treating problems of impaired growth, development, metabolism, stress, and reproduction.

Finally, the LACC proteins of the present invention including ChR2 can be used to screen for drugs that alter slow signal transduction processes in cells, revealing treatments for chronic disease processes ranging from cancer to depression. In particular, immune cells respond to ongoing patterns of Ca+2 influx with a variety of long-lasting changes, which can lead to strengthening or weakening of immune responses, or even possibly autoimmune symptoms. Cancer cells also express ion channels, and may respond to electrical activity with altered proliferation. Neural stem cells respond to depolarization and Ca+2 influx by differentiating into neurons; activating stem cells expressing LACC proteins with light can then enhance survival and incorporation into mature tissues, a step in generation of functional brain and other tissue.

In a preferred embodiment of a method of drug screening, the stem cell line expressing a LACC protein of the present invention such as ChR2 can be used to optically control tissue repair, and illumination of these stem cells with light results in CREB phosphorylation, a critical step in enhancing their transformation into neurons.

Another preferred embodiment is a method of drug screening comprises making a human embryonic stem (ES) cell line with ChR2 under a stem-cell specific promoter to build cells which differentiate under optical control. Expression of ChR2 in such cells allows discovery of drugs which alter the activity-dependent progress of cellular life and death amidst their environments.

Using the methods of the present invention, cells can be forced to change developmental fate via remote control, and a drug screening tool where this is possible allows the discovery of new molecules that manipulate such long term effects of cell proliferation, differentiation, and apoptosis. In all of these scenarios, specific cell populations will be light-addressable on rapid timescales, allowing the screening of many aspects of cellular function.

Figure 11:
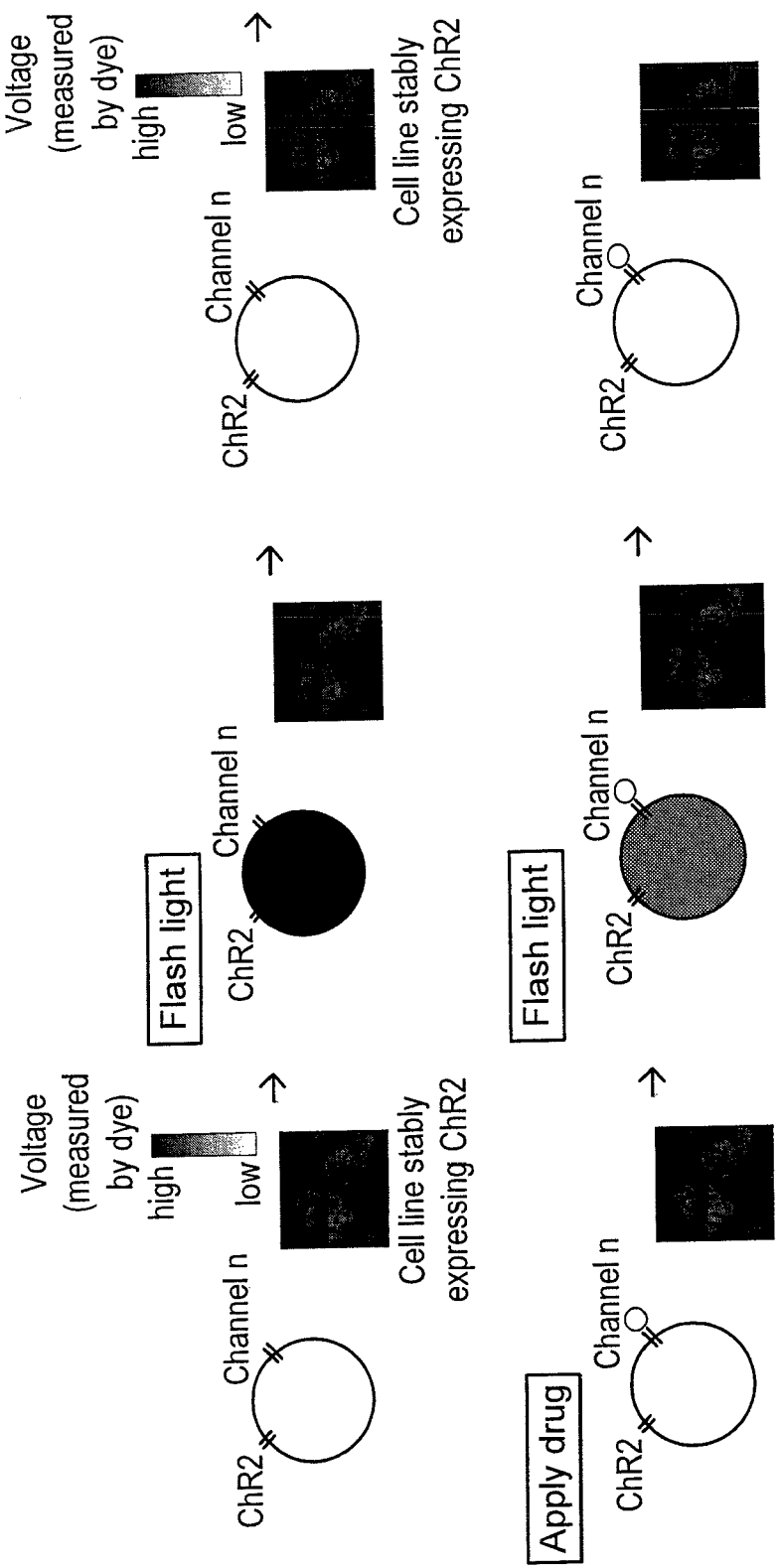
FIG. 11 illustrates an embodiment of one of the methods of the invention.

These techniques are suitable for screening for drugs that modulate ion channel function (blocking or facilitating ion channel function—either by blocking the pore, affecting the gating, or affecting the open channel). FIG. 11 illustrates one example of the methods for screening drugs. First, the baseline electrical activity of the ion channel is measured by flashing the light and observing the depolarization. The fluorescence of the cells will return to its original value after the light is off. Then a drug is applied, for example, by pipetting in the drug (or flowing in through a microfluidic channel). Finally, the light is re-flashed and the electrical activity of the ion channel is measured. This technique can be used in combination with the whole-cell patch clamp technique, wherein an electrode is placed up to a cell, suction is applied to break into the cell, and to record the activity of the cell expressing an ion channel before and after the application of a drug. Examples of drugs that can be screen according to the methods described herein include, but are not limited to, antidepressants, antipsychotics, calcium antagonist, antiepilecticts, as well as drugs to treat OCD, Alzheimer's, Parkinson, obesity, addiction, chronic pain, muscle and heart disorders.

One embodiment of a method for drug screening is as follows:

1) express a light activated channel protein, preferably Channelrhodopsin, in a cell line;
2) express an ion channel of interest ("channel n") in the same cell line;
3) label the cells with a voltage sensitive dye (or other suitable indicator, such as those described below);
4) expose said cells to light, and record the fluorescence of the voltage sensitive dye;
5) expose said cells to a candidate compound that possibly modulates the function of channel n;
6) expose said cells to light a second time, and record the fluorescence of the voltage sensitive dye.

Preferably, the modulation of the light activated channel protein is related to the modulation of the channel n. For example, activation of the light activated channel protein causes an activation of channel n. This co-relation in activity can be direct or indirect. The co-relation can be via a signal transduction pathway. The co-relation in activity can be directly proportional to each other or inversely proportional to each other.

If the fluorescence is greater during step (6) than step (4), presumably the candidate drug facilitates channel function. If the fluorescence is smaller during step (6) than step (4), presumably the candidate drug diminishes channel function. If the fluorescence is equal in steps (4) and (6) (allowing for any bleaching of the dye), then the drug does not affect channel function. In this way, drugs that affect channel function can be detected rapidly. FIG. 11 illustrates one example in which the drug is a negative modulator of channel function After preparation of the cell line in steps (1) and (2), the cell line would suffice for the screening of many (perhaps millions of) drugs, which modulate channel n. Steps (4), (5), and (6) can take place in a robotic device that moves a 384-well plate into the focus of an optical beam. The wells of the plate could all contain the same cell line, facilitating the screening of drugs that affect a particular channel ("high throughput target screening," see below), or each well could contain cells of a different cell line, facilitating the screening of one drug against many different channels ("screening against side effects," see below).

A voltage sensitive dye is preferred due its fast kinetics, but other dyes (e.g., a calcium-sensitive dye in the case that channel n is a calcium channel) could also serve to indicate whether channel function is modulated by the drug. Genetically encoded indicators of voltage or calcium may also be useful for reading out the activity of the cell (e.g., FLASH, GCaMP2, cameleon, etc.). In this case, these indicators would be stably expressed in the cell line as well. Other methods of reading out whether the drug had an effect are also useful—e.g., immunostaining for the phosphorylation of a site that is phosphorylated during or after periods of ion channel activity.

For drug screening, it is preferred to have an optical imaging device containing 1) a light source (light-emitting diode (LED), lamp, laser) for illuminating the cell expressing Channelrhodopsin and driving a change in cell voltage, 2) a light source for illuminating a dye or indicator, possibly the same light source as used for driving the voltage change, and 3) a switch for alternating between the two light sources or a beamsplitter for simultaneous non-interfering delivery of both kinds of light. The fluorescence of the dye or indicator is typically measured by a sensor (CCD camera, PMT, or photodiode). This kind of device is useful for ion channel drug screening, as described above. The device itself may also consist of a robotic arm for moving a plate (e.g., a 384-well plate) through the arena where the light sources and sensor are present. This kind of combined light source/imaging device has also diagnostic applications. For example, taking cells from a patient, expressing Channelrhodopsin in them, and then exposing them to light, could be used to detect patient-specific ion channel syndromes in biopsy samples or in cells of the circulatory system.

The methods described herein are preferably performed with channelrhodopsin, but any suitable light-activated cation channel can be used.

Yet another aspect of the invention is methods for high-throughput target screening. In one embodiment, high-throughput target screening comprises a plate reader that moves wells containing cells of interest into the optical stimulation/readout area, and then performs the methods described above and illustrated in FIG. 11. Then the machine moves the plate to enable the next well to be flashed, in turn. Examples of well plates include 96-, 384, 1526-well plates. In one embodiment, the high-throughput target screening methods of the invention can analyze up to about 2,000 drugs per day per setup. In another embodiment, the high-throughput target screening methods of the invention can analyze up to about 2,500,000 drugs per year per 5 setups.

In another embodiment, high-throughput target screening comprises a chip-based system. A chip-based system can enable sequential rather than parallel testing of compounds on ion channels by high-speed scanning of a single cell across a laminar stream of solution environments created in the microfluidic chips. The scanning of the microfluidic chip, causing a cell to sample the discrete zones of drug solutions, is controlled by a computer controlled motorized scan stage. The microfluidic chips, for example, can have eight-channel, 16-channel, 48-channels or more for high-throughput analysis.

In another embodiment, high-throughput target screening comprises a cell sorting device that includes an array of discrete locations for capturing cells traveling along a fluid flow. The discrete locations can be arranged in a defined pattern across a surface such that the discrete sites are also addressable and contain discrete zones of drug solution. Examples of surfaces that may be used for creating arrays of cells in discrete sites include, but are not limited to, cellulose, cellulose acetate, nitrocellulose, glass, quartz or other crystalline substrates such as gallium arsenide, silicones, metals, semiconductors, various plastics and plastic copolymers, cyclo-olefin polymers, various membranes and gels, microspheres, beads and paramagnetic or supramagnetic microparticles.

Yet another aspect of the invention is methods for screening against side effects. This method allows for screening for drugs that selectively affect one ion channel, but do not affect other ion channels. This screening against individual ion channels allows for screening to predict potential side effects.

As an example of screening for side effects: many channels are expressed differentially in the heart vs. the brain. By screening for drugs that differentially bind to channels in the brain, but not the heart, it is possible to find neuropsychiatric drugs that don't affect heart function. Especially important for heart function are calcium channels, HERG channels, other potassium channels, and other ion channels that affect the rhythmicity or amplitude of the heartbeat.

Prosthetic Devices

Another aspect of the invention is the use of the methods and compositions described herein in prosthetic devices. Blindness, deafness, and other sensory deficits affect millions of people worldwide, severely impacting their quality of life. Channelrhodopsin, targeted to somatic cells in the human patient, opens up a new class of sensory prostheses. For example, some forms of blindness destroy photosensor function, but leave signal processing in downstream neurons intact. In such diseases, such as macular degeneration or retinitis pigmentosa, targeting Channelrhodopsin to retinal ganglion cells (for example, by injecting viruses expressing channelrhodopsin into the retinal cell layers inside the eye) could enable restoration of visual function. In such patients treated with channelrhodopsin targeted to retinal ganglion cells, the retinal ganglion cells would themselves become photosensitive, enabling vision with resolution comparable to the native eye, and preferably not requiring invasive technology beyond that point. Channelrhodopsin is sufficiently sensitive to detect sunlight (power ~1 kW/m^2). Alternatively, the Channelrhodopsin can be targeted to amacrine cells or bipolar cells to enable vision. It is also possible that expressing channelrhodopsin in a retinal cell, accompanied with a projection device that would amplify the ambient light, would enable vision indoors or in low-light conditions.

In another embodiment, in many age- and experience-related forms of deafness, hair cells are lost, but downstream neurons are intact. Expressing Channelrhodopsin in spiral ganglion cells (i.e., eight nerve neurons) would enable activation of these cells with light. Cochlear implants currently stimulate all the cells of the cochlea with a single electrode or at most a few electrodes, and do not attempt to recapitulate any of the spatial distribution of sensory afferents in the cochlea. By inserting a device containing 1) a microphone to detect sound, 2) a microprocessor to analyze the frequency components of the sound and convert them to LED signals, and 3) multiple LEDs for emitting light in a spatially patterned fashion, into the cochlea, a tonotopically-mapped stimulator could be created, which would drive different frequencies of sound perception simply by targeting the light to appropriate cells.

In yet another embodiment, central nervous system neurons in a human are infected with virus expressing Channelrhodopsin (or otherwise come to express Channelrhodopsin), these neurons become capable of responding to light. This gene therapy approach allows optical stimulation of neuronal targets in the brain. If the targeted neurons are in sensory cortex, this opens up the possibility of a new kind of cortical sensory prosthesis. If the targeted neurons are in the frontal cortex or other parts of the brain, it is in possible that these light-sensitive neurons permit modulation of emotion or cognition. If the targeted neurons were in the spinal cord, it is possible that neurons that inhibit painful stimuli could be driven by light. In general, this gene therapy approach opens up a new kind of generalized prosthetic, in which light is converted into neural activity, in defined parts of the nervous system.

One embodiment of a prosthetic device, is for implanted cells that are engineered to secrete compounds and to respond to light, and also for hunting for neural-circuit level targets in the intact animal brain, it may be very useful to have an implantable or head-mounted LED, or other small light source. Such a light source could be implanted under the skin, under the skull, deep within the brain, or deep within another organ of interest, in which Channelrhodopsin-expressing cells are also located (either exogenously introduced, or endogenously located and targeted with a virus). This device could be used for stimulating ChR2 in cells located directly adjacent to the light source. For the example of the cochlear implant, a strip of LEDs, each individually controllable, could be useful. For the example of the cortical implant, a 2-dimensional array of LEDs could be useful. For the example of an insulin-secreting cell located under the skin, a wearable blue LED on a bracelet, powered by a battery, could be useful.

In some embodiments, for medical applications, the LEDs are remotely powered. A remotely-powered LED could be made by combining an LED in a closed-loop series circuit with an inductor. This would allow radiofrequency (RF) energy or rapidly changing magnetic fields (e.g., delivered by a transcranial magnetic resonance (TMS) coil) to temporarily power-up the inductor, and thus the connected LED, allowing local delivery of light, even deep in a brain structure. Such a device could be implanted under the skin, under the skull, deep within the brain, or deep within another organ, of interest in which Channelrhodopsin-expressing cells are also located (either exogenously introduced, or endogenously located and targeted with a virus). Then a device that can remotely deliver RF or magnetic energy could be placed nearby, or worn on the patient, for activating the implanted device.

Biochemical Modifications

Another aspect includes biochemical modifications of light activated channels, such as Channelrhodopsin. Such modifications are typically performed to target Channelrhodopsin to different parts of a cell. Fusing channelrhodopsin to a targeting sequence of DNA, so that the resultant protein contains both channelrhodopsin and the targeting peptide, could be used to send Channelrhodopsin to the presynaptic terminal, the postsynaptic terminal, the nucleus, or other intracellular compartments. Such targeting sequences include PDZ domains, glutamate and GABA receptor C-terminal sequences, ion channel c-terminal sequences, presynaptic scaffolding targeting sequences, and other targeting sequences. These versions of Channelrhodopsin could be used to trigger specific intracellular signaling events, including those important for neuroprotection, memory, or other enduring signaling functions.

In a combinatorial fashion, these reagents could complement the other applications of Channelrhodopsin. For example: these reagents could be useful for drug screening (e.g., finding drugs that modulate the function of a channel in a particular subcellular compartment). These reagents could also be useful for prosthetic devices (e.g., driving activity on the dendrites of a neuron, to more closely mimic natural synaptic activity).

The methods and devices are described herein with LEDs, but a small laser, or a fiber optic cable that carries light from an external source (a xenon or mercury lamp) can also be used. Preferred light sources used to illuminate the Channelrhodopsin-expressing cells have the following properties:
- stimulation times tunable from 0-25 ms, or even longer
- brightnesses tunable in the range 0-10 mW/mm^2, or even higher
- wavelengths in the range 440-490 nm, or broader depending on the identity of the light-activated channel Articles of Manufacture In another aspect of the invention, articles of manufacture containing the compositions described herein (e.g. a nucleic acid comprising an LACC sequence or a LACC protein-expressing cell) are provided. The article of manufacture comprises a container and a label. Suitable containers include, for example, bottles, vials, syringes, plates, and test tubes. The containers may be formed from a variety of materials such as glass or plastic. Suitable packaging and additional articles for use (e.g., measuring cup for liquid preparations, foil wrapping to minimize exposure to air, dispensers, and the like) are known in the art and may be included in the article of manufacture.

In one embodiment, the container is a 96-, 384-, and 1526-well plate containing different cells of interest in each well, for example, prefrozen in a protective medium (e.g. medium containing 20% DMSO). The plates can be shipped in dry ice and store upon receipt at −80 degrees Celsius for short term storages. Alternatively, the plates are stored in liquid nitrogen for long term storage. This plate fit into a plate-reader/motorized stage device as the ones described above or a regular plate reader known in the art.

In one embodiment, the container holds a composition that is effective for treating a disease condition and may have a sterile access port (for example the container may be an intravenous solution bag or a vial having a stopper pierceable by a hypodermic injection needle). The active agent in the composition is the compositions of the invention described herein (e.g. a nucleic acid comprising an LACC sequence or a LACC protein-expressing cell). The article of manufacture can further comprise, within the same or a separate container, another agent such as a therapeutic agent that is co-administered with the compositions of the invention and optionally a pharmaceutically acceptable buffer, such as phosphate-buffered saline, Ringer's solution and dextrose solution.

The label on, or associated with, the container indicates instructions to use the composition, for instance, the container may indicated that the composition is used for treating a disease condition of choice or for screening compounds or screening compound's side effects. The containers described herein may further include other materials desirable from a commercial and user standpoint, including other buffers, diluents, filters, needles, syringes, and package inserts with instructions for use.

It is understood that the examples described herein in no way serve to limit the true scope of this invention, but rather are presented for illustrative purposes. All references and sequences of accession numbers cited herein are incorporated by reference in their entirety.

EXAMPLES

Plasmid Constructs.

The ChR2-YFP gene was constructed by in-frame fusing EYFP (Clontech) to the C-terminus of the first 310 amino acid residues of ChR2 (GeneBank accession no. AF461397) via a NotI site. The lentiviral vector pLECYT was generated by PCR amplifying ChR2-YFP with primers:

5'-GGCAGCGCTGCCACCATGGATTATGGAGGCGCCCTGAGT-3'
and

5'-GGCACTAGTCTATTACTTGTACAGCTCGTC-3' and ligating into pLET (gift from Eric Wexler and Theo Palmer, Stanford University) via the AfeI and SpeI restriction sites. The plasmid was amplified and then purified using Qiagen MaxiPrep kits (Qiagen).

Viral Production.

VSVg pseudotyped lentiviruses were produced by triple-transfection of 293FT cells (Invitrogen) with pLECYT, pMD.G, and pCMVdeltaR8.7 (gifts from Eric Wexler and Theo Palmer) using Lipofectamine 2000. The lentiviral production protocol is same as previously described[42] except for the use of Lipofectamine 2000 instead of calcium phosphate precipitation. After harvest, viruses were concentrated by centrifuging in a SW28 rotor (Beckmann Coulter) at 20,000 rpm for 2 h at 4° C. The concentrated viral titer is determined via FACS sorting to be between $5\times10^8$ and $1\times10^9$ IU/mL.

Hippocampal Cell Culture.

Hippocampi of postnatal day 0 (P0) Sprague-Dawley rats (Charles River) were removed and treated with papain (20 U/ml) for 45 min at 37° C. The digestion was stopped with 10 ml of MEM/Earle's salts without L-glutamine along with 20 mM glucose, Serum Extender (1:1000), and 10% heat-inactivated fetal bovine serum containing 25 mg of bovine serum albumin (BSA) and 25 mg of trypsin inhibitor. The tissue was triturated in a small volume of this solution with a fire-polished Pasteur pipette, and ~100,000 cells in 1 ml plated per coverslip in 24-well plates. Glass coverslips (prewashed overnight in HCl followed by several 100% EtOH washes and flame sterilization) were coated overnight at 37° C. with 1:50 Matrigel (Collaborative Biomedical Products, Bedford, Mass.). Cells were plated in culture medium: Neurobasal containing 2× B-27 (Life Technologies) and 2 mM Glutamax-I (Life Technologies). One-half of the medium was replaced with culture medium the next day, giving a final serum concentration of 1.75%. No all-trans-retinal was added to the culture medium or recording medium for any of the experiments here described. However, B27 contains small amounts of retinal derivatives like retinyl acetate, which may have assisted with ChR2 function. Additional supplementation with all-trans-retinal, or its precursors, may assist in the application of ChR2 to the studying of intact circuits.

Viral Infection.

Hippocampal cultures were infected on d.i.v. 7 using 5-fold serial dilutions of lentivirus ($1\times10^6$ IU/mL). Viral dilutions were added to hippocampal cultures seeded on coverslips in 24 well plates and then incubated at 37° C. for 7 d before recording using patch-clamping technique.

Confocal Imaging.

Images were acquired on a Leica TCS-SP2 LSM confocal microscope using a 63× water-immersion lens. Cells expressing ChR2-YFP were imaged live using YFP microscope settings, in Tyrode's solution containing (in mM): NaCl, 125; KCl, 2; $CaCl_2$, 3; $MgCl_2$, 1; glucose, 30; and HEPES, 25 (pH 7.3 with NaOH). Propidium iodide (PI; Molecular Probes) staining was carried out on live cells by adding 5 µg/mL PI to the culture medium for 5 minutes at 37° C., washing twice with Tyrode solution, and then counting fluorescent and non-fluorescent cells immediately. Coverslips were then fixed for 5 minutes in PBS plus fresh 4% paraformaldehyde, permeabilized for 2 minutes with PBS plus 0.1% Triton X-100, and then immersed for 5 minutes in 5 µg/mL PI for observation of any pyknotic nuclei. At least eight different fields were examined per coverslip.

Electrophysiology and Optical Methods.

Cultured hippocampal neurons were recorded at approximately d.i.v. 14, 7 days after infection. Neurons were recorded using the whole-cell patch clamp technique, using Axon Multiclamp 700B (Axon Instruments, Inc.) amplifiers on an Olympus IX71 inverted scope equipped with a 20× objective lens. Borosilicate glass (Warner) pipette resistances were on average 4 MΩ, range 3-8 MΩ. Access resistance was 10-30 MΩ and was monitored throughout the recording. Intracellular solution consisted of 97 potassium gluconate, 38 KCl, 0.35 EGTA, 20 HEPES, 4 magnesium ATP, 0.35 sodium GTP, 6 NaCl, and 7 phosphocreatine (pH 7.25 with KOH). Neurons were perfused in Tyrode's solution, described above. All experiments were performed at room temperature (22-24° C.). For all experiments except for the synaptic transmission data shown in FIGS. 4b and 4c, we patched fluorescent cells immersed in Tyrode solution containing 5 µM NBQX and 20 µM gabazine to block synaptic transmission. Photocurrents were measured while holding neurons in voltage clamp at −65 mV. Recovery from inactivation was measured by measuring photocurrents while illuminating neurons with pairs of pulses lasting 500 ms each, separated by periods of darkness lasting 1-10 seconds.

Spiking was measured while injecting current to keep the voltage of the cell at approximately −65 mV (holding current ranging from 0 pA to 200 pA). For the synaptic transmission experiments, we patched nonfluorescent neurons near ChR2-expressing neurons, immersed in Tyrode solution containing either 20 µM gabazine to isolate just the excitatory postsynaptic response, or in 5 µM NBQX to isolate just the inhibitory postsynaptic response. To confirm whether the evoked potentials were indeed synaptically driven, after synaptic stimulation we blocked all postsynaptic receptors with solution containing both 20 µM gabazine and 5 µM NBQX, and rephotostimulated.

pClamp 9 software (Axon Instruments) was used to record all data and to operate the MultiClamp 700B amplifier, and a Sutter DG-4 ultrafast optical switch with 300W xenon lamp (Sutter Instruments) was used to deliver the light pulses for ChR2 activation. A standard Endow GFP excitation filter (excitation filter HQ470/40x, dichroic Q495LP; Chroma) was used for delivering blue light for ChR2 activation, in the bandwidth 450-490 nm. YFP was visualized with a standard YFP filter (excitation HQ500/20×, dichroic Q515LP, emission HQ535/30m; Chroma). Through a 20× objective lens, power density of the blue light was 8-12 mW/mm2, as measured with a silicon power meter (Newport). Pulse sequences were synthesized by custom software written in MATLAB (MathWorks) and then exported through pClamp 9 via a Digidata input/output board (Axon), attached to a PC.

Poisson trains were 8 seconds long, with Poisson parameter λ=100 or 200 ms. For Poisson trains, a 10 ms-minimum refractory period was imposed between light pulses, for biophysical realism.

Membrane resistance was measured in voltage clamp mode with 20 mV pulses lasting 75 ms, and repeated every 3 seconds. Spike rates due to direct current injection were measured with pulses of 300 pA current lasting 0.5 seconds.

Data Analysis.

Data was analyzed automatically using Clampfit (Axon) and custom software written in MATLAB. Spikes were extracted by looking for crossings of the voltage above a threshold (typically 60 mV above resting potential), and latencies were measured from the onset of the light pulse to the spike peak. Extraneous spikes were measured as the number of extra spikes after a single light pulse, plus any spikes occurring later than 30 ms after the onset of a light pulse.

Jitter was calculated as the standard deviation of spike latencies, measured either throughout the spike train (when gauging reliability throughout a train), or for the same spike across different trains (when gauging reliability across trials, or across neurons). For all jitter analyses, light pulses that did not elicit a spike in a particular neuron were ignored for the analysis of jitter of that neuron. For the across-neurons jitter analysis shown in FIG. 2h, light pulses that did not elicit spikes in all 7 neurons were ignored (leaving 31/59 light pulses for the λ=100 stimulus, and 30/46 light pulses for the λ=200 stimulus).

Example 1

Figure 1B:
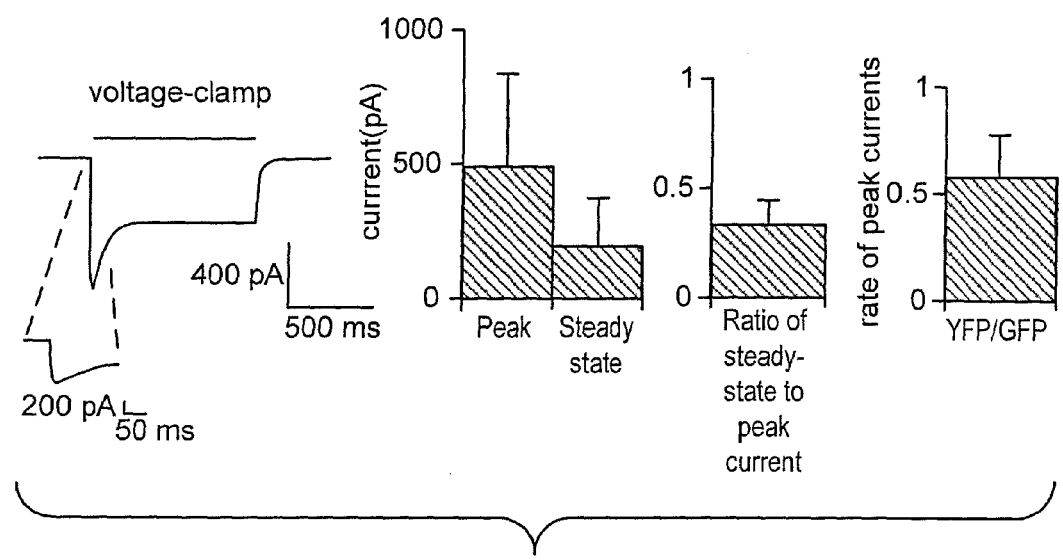
FIG. 1(b) shows b, Inward current in voltage-clamped neuron (left) evoked by 1 second of excitation light (indicated by lines throughout figures), with population data (middle; mean±standard deviation plotted throughout figures; n=18). The figure also shows that light through a YFP filter evokes smaller currents (right; n=5).
Figure 1C:
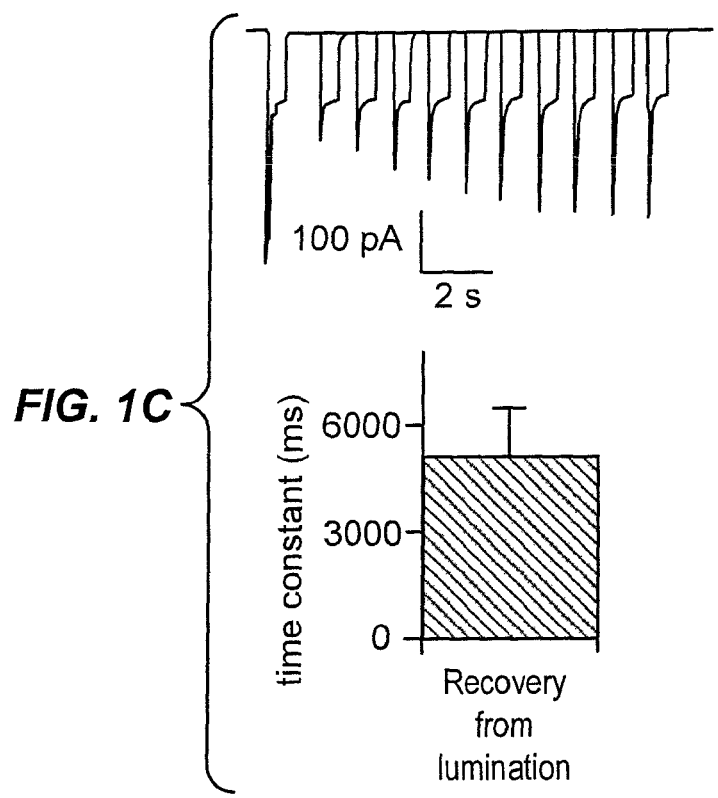
FIG. 1(c) shows currents in a hippocampal neuron illuminated as in FIG. 1(b), in response to light pulses.

To obtain stable and reliable ChR2 expression for coupling light to neuronal depolarization, we constructed lentiviruses containing a ChR2-YFP fusion protein for genomic modification of neurons. Infection of cultured rat CA3/CA1 neurons led to appropriately membrane-localized and well-tolerated expression of ChR2 for days to weeks after infection (FIG. 1a). There was no evidence of toxicity due to the expressed protein, even at high fusion protein expression levels. Whole-cell voltage-clamp recording of neurons showed that conventional GFP illumination in the bandwidth 450-490 nm (300W xenon lamp (Sutter DG-4), via Chroma excitation filter HQ470/40×) induced depolarizing currents with fast rise rates—reaching a maximal rise rate of 160+111 pA/ms within 2.3+1.1 ms after the onset of the light pulse (mean±standard deviation reported throughout, n=18; FIG. 1b, left). Mean whole-cell inward currents were large, 496 pA±336 pA at peak and 193 pA±177 pA at steady-state (FIG. 1b, middle). In control experiments, light-evoked responses were never seen in cells expressing YFP alone (data not shown). Consistent with the known excitation spectrum of ChR2[20], illumination of ChR2-expressing neurons with YFP-spectrum light in the bandwidth 490-510 nm (300W xenon lamp filtered with Chroma excitation filter HQ500/20×) resulted in smaller currents than those evoked with the GFP filters (FIG. 1b, right). Despite the inactivation of ChR2 with sustained light exposure (FIG. 1b and ref.[20]), we observed rapid recovery of peak ChR2 photocurrents in neurons (FIG. 1c; τ=5.1+1.4 seconds; recovery trajectory fit with Levenberg-Marquardt algorithm; n=9). This rapid recovery is consistent with the well-known stability of the Schiff base (the lysine in transmembrane helix 7, which binds retinal) in microbial-type rhodopsins, and the ability of retinal to re-isomerize to the all-trans ground state in a dark reaction without the need for other enzymes. In addition to the short-term recovery of peak photocurrents shown above, light-evoked current amplitudes were also stable over long timescales, remaining unchanged in patch-clamped neurons throughout an hour of pulsed light exposure (data not shown), confirming at the functional level the lack of toxicity suggested by the confocal images (FIG. 1a). Thus ChR2 can mediate rapid and sustainable photocurrents of large amplitude, without detectable adverse side effects.

Example 2

Figure 1D:
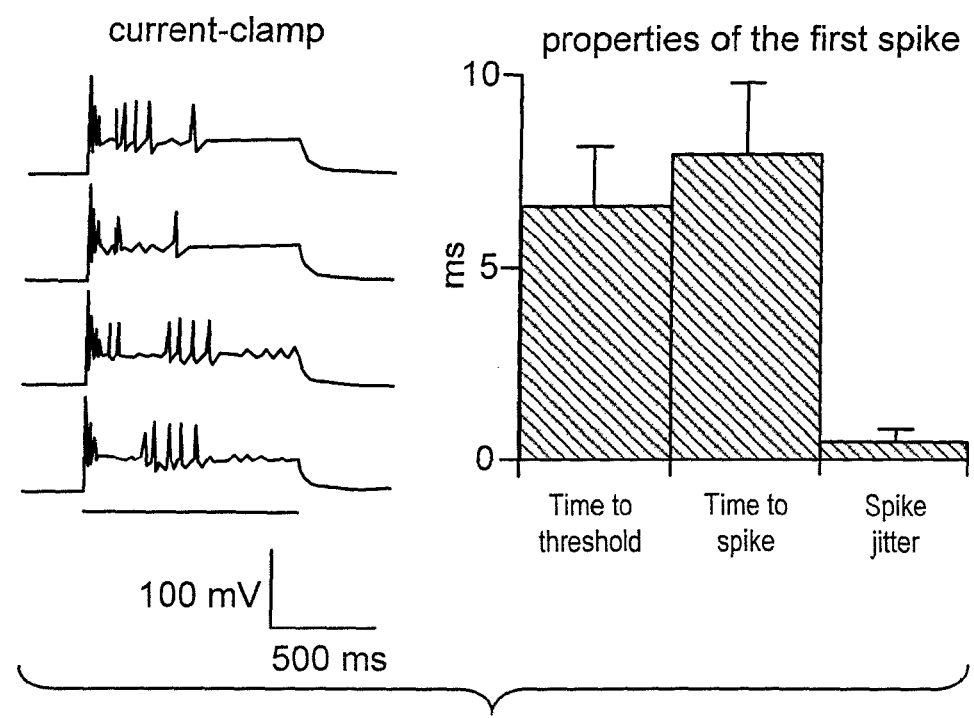
FIG. 1(d) has voltage traces showing membrane depolarization and spikes in a current-clamped hippocampal neuron (left) evoked by 1 second periods of blue light. Right, properties of the first spike elicited (n=10), showing latency to spike threshold, latency to spike peak, and jitter of spike peak time.

We examined whether ChR2 could drive actual depolarization of neurons held in current-clamp mode, with the same steady illumination protocol we used for eliciting ChR2-induced currents (FIG. 1d, left). Early in an epoch of steady illumination, single neuronal spikes were rapidly and reliably elicited (8.0+1.9 ms latency to spike peak, n=10; FIG. 1d, right), consistent with the fast rise times of ChR2 currents described above. However, for these cells, at these specific conditions, any subsequent spikes elicited during steady illumination were poorly timed (FIG. 1d, left). Thus, for this particular sample, steady illumination was not adequate for controlling the timing of ongoing spikes with ChR2, despite the reliability of the first spike. Earlier patch-clamp studies using somatic current injection showed that spike times were more reliable during periods of rapidly rising membrane potential than during periods of steady high-magnitude current injection. This is consistent with our finding that steady illumination evoked a single reliably timed spike, followed by irregular spiking.

Example 3

Figure 1E:
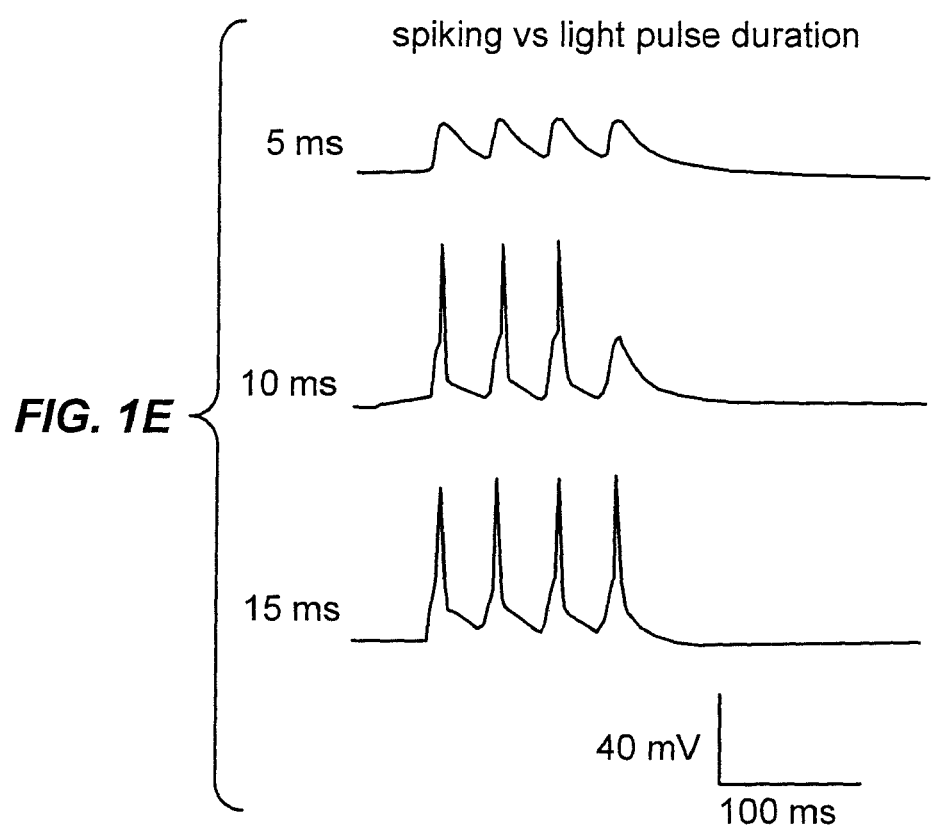
FIG. 1(e) has voltage traces in response to brief light pulse sequences, with pulses lasting 5 ms (top), 10 ms (middle), and 15 ms (bottom).

We found that the single spike reliably elicited by steady illumination had extremely low temporal jitter from trial to trial (FIG. 1d, right; 0.5+0.3 ms; n=10 neurons). This observation led us to devise a pulsed-light paradigm, which takes advantage of the low jitter of the single reliable spike evoked at light pulse onset. But in order for such a pulsed-light paradigm to work, the conductance and kinetics of ChR2 would have to permit peak currents of sufficient amplitude, during light pulses shorter than the desired interspike interval. Indeed, using fast optical switching, we found that multiple pulses of light with interspersed periods of darkness could elicit reliable and well-timed trains of spikes (FIG. 1e; shown for 25 Hz trains of four pulses). FIG. 1e highlights the fact that longer light pulses evoke single spikes with greater probability than short light pulses. The ability to easily alter light pulse duration with fast optical switching suggests a straightforward method for eliciting spikes even in multiple neurons possessing different ChR2 current densities, by simply increasing the light pulse duration until single spikes are reliably obtained in all the neurons being illuminated. Rapid modulation of light power would also allow for this kind of control. In the experiments described here, we used light pulse durations of either 5, 10, or 15 ms (n=13 high expressing neurons fired reliable spikes; n=5 low-expressing neurons fired reliable subthreshold depolarizations). Thus, the nonlinear nature of neuronal spike production allow us to elicit spikes reliably, simply by increasing the light energy delivered to the ChR2-expressing neuron until the resultant voltage deflection is above the threshold for spiking. Without the use of brief light pulses, however, it is possible that the fast kinetics of ChR2 would not serve as usefully in the control of reliable spike induction: this highlights the need for optical equipment to be matched to the bandwidth of the photostimulation reagent.

Example 4

Figure 2A:
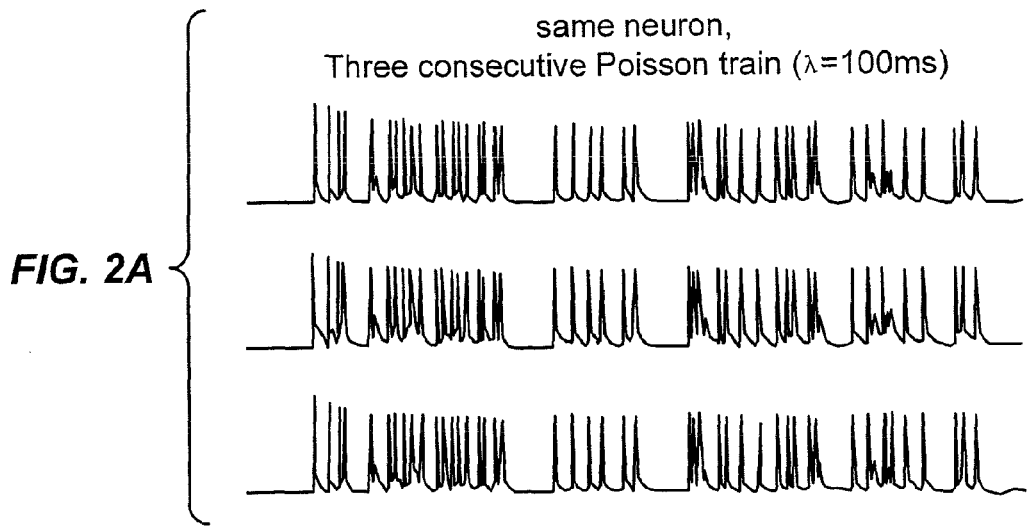
FIG. 2(a) has voltage traces showing spikes in a current-clamped hippocampal neuron, in response to three deliveries of a Poisson train of light pulses.
Figure 2B:
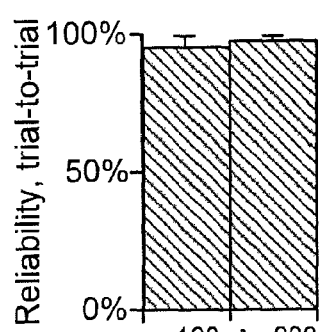
FIG. 2(b) shows trial-to-trial reliability of light evoked spike trains, as measured by comparing the presence or absence of a spike in two repeated trials of the same Poisson train delivered to the same neuron.
Figure 2C:
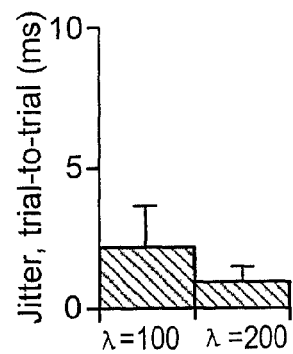
FIG. 2(c) shows trial-to-trial jitter of the light-evoked spike trains.
Figure 2D:
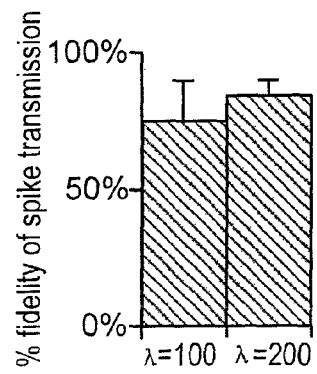
FIG. 2(d) shows the percent fidelity of spike transmission throughout the entire 8-second Poisson train.
Figure 2E:
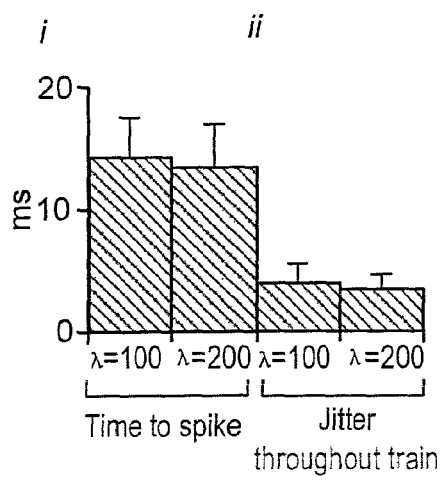
FIG. 2(e) shows latency of the spikes throughout each light pulse sequence (i), and jitter of spike times throughout the train (ii).

The millisecond-scale control discovered herein raised the prospect of generating arbitrarily defined, even naturalistic spike trains (such as Poisson trains, used commonly to model natural activity) in neurons by remote optical control. FIG. 2a shows spike trains in a hippocampal neuron in response to three deliveries of the same Poisson distributed series of light pulses (here shown for a light pulse series 59 pulses long, each lasting 10 ms; Poisson parameter $\lambda$=100 ms). These optically-driven spike trains were quite consistent across repeated deliveries of the same series of light pulses: on average, >95% of the light pulses in a series elicited spikes during one trial if and only if they elicited spikes on a second trial, for both the $\lambda$=100 ms series shown in FIG. 2a, and a $\lambda$=200 ms series comprising 46 spikes (FIG. 2b; n=7 neurons). Following the strategy of increasing light pulse duration to the point of reliable spiking, we used trains of light pulses lasting 10 ms each for 4 of the 7 neurons, and trains of light pulses lasting 15 ms for the other 3 (for the analyses of FIG. 2, all data were pooled). The trial-to-trial jitter was very small across repeated deliveries of the same Poisson series of light pulses (2.3+1.4 ms and 1.0+0.5 ms for $\lambda$=100 and $\lambda$=200 respectively; FIG. 2c). Throughout extended pulse series, the efficacy of eliciting spikes throughout the train was maintained (76% and 85% percent of light pulses successfully evoked spikes, respectively; FIG. 2d). The latencies to spike after light pulse onset were also consistent throughout the series of pulses (14.3+3.1 ms and 13.3+3.4 ms respectively; FIG. 2e). Finally, spike jitter remained remarkably small throughout the train (3.9+1.4 ms and 3.3+1.2 ms; FIG. 2e). Hence, pulsed optical activation of ChR2 can elicit precise, repeatable spike trains in a single neuron, over time.

Example 5

Figure 2F:
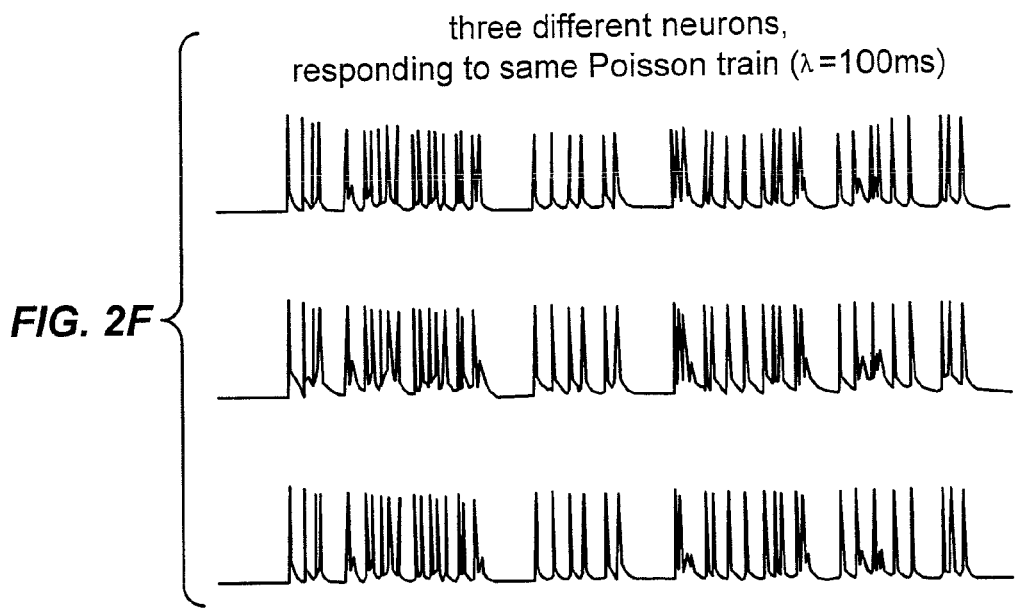
FIG. 2(f) has voltage traces showing spikes in three different hippocampal neurons, in response to the same temporally patterned light stimulus as used in FIG. 2(a).
Figure 2G:
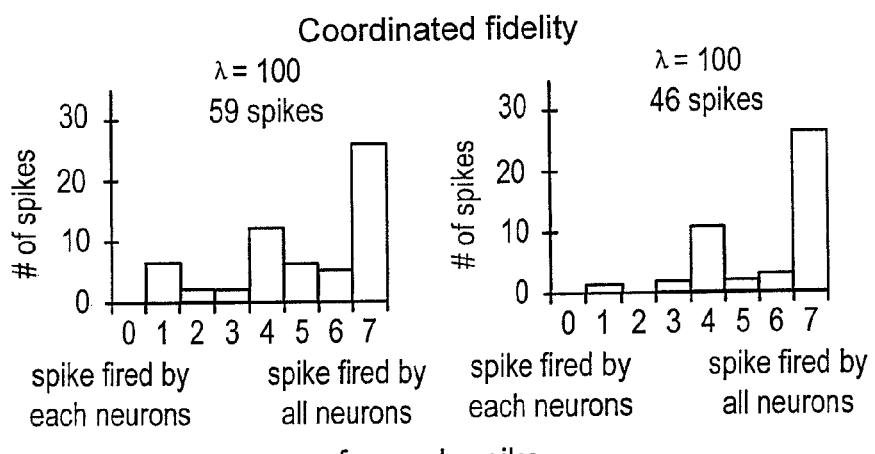
FIG. 2(g) has a histogram showing how many of the 7 neurons spiked in response to each light pulse in the Poisson train.
Figure 2H:
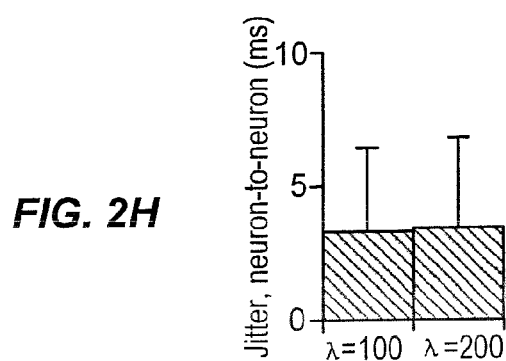
FIG. 2(h) shows neuron-to-neuron jitter of spikes evoked by light stimulation.

Even across different neurons, activation of ChR2 by defined series of light pulses could elicit the same spike train with strikingly high fidelity (shown for three hippocampal neurons in FIG. 2f). Although the heterogeneity of individual neurons—for example, in their membrane capacitance (68.8+22.6 pF) and resistance (178.8+94.8 MΩ)—might be expected to introduce significant variability in their integrative electrical properties, the strong nonlinearity inherent in the coupling of light to spiking overcame this variability. Indeed, different neurons responded in similar ways to a given light pulse series, with 80-90% of the light pulses in a train eliciting spikes in at least 4 of the 7 the neurons examined (FIG. 2g). Moreover, spikes had very low temporal jitter when measured for the same light pulse series delivered to different neurons (3.4+1.0 ms and 3.4+1.2 ms for $\lambda$=100 and $\lambda$=200 respectively; FIG. 2h). Remarkably, this across-neuron jitter (FIG. 2h) was identical to the within-neuron jitter, measured throughout the light pulse series (FIG. 2e). Thus, heterogeneous populations of neurons can be controlled in concert, with practically the same precision observed for the control of single neurons over time.

Example 6

Figure 3A:
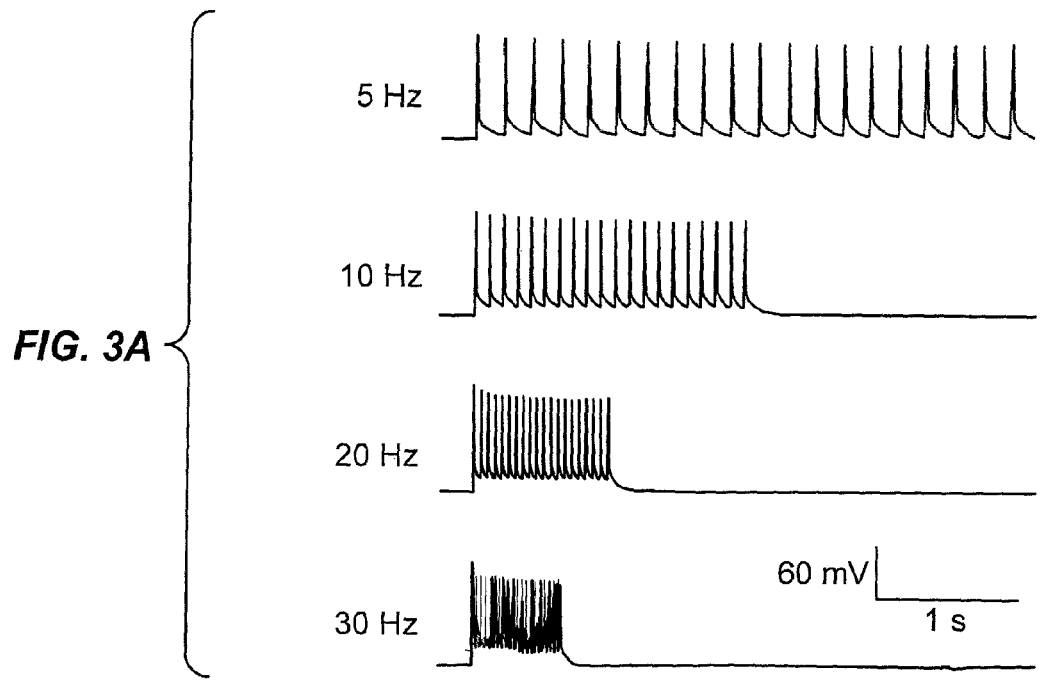
FIG. 3(a) has voltage traces showing spikes in a current-clamped hippocampal neuron evoked by 5, 10, 20, or 30 Hz trains of light pulses.
Figure 3B:
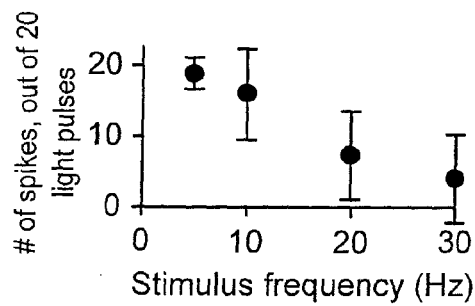
FIG. 3(b) has population data showing the number of spikes (out of 20 possible) evoked in current-clamped hippocampal neurons.
Figure 3D:
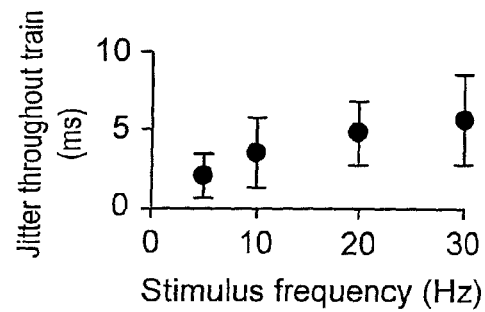
FIG. 3(d) shows jitter of spike times throughout the train of light pulses for the experiment described in FIG. 3(b).
Figure 3C:
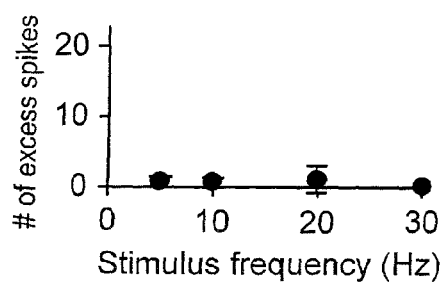
FIG. 3(c) shows the number of extraneous spikes evoked by the trains of light pulses, for the experiment described in FIG. 3(b).
Figure 3E:
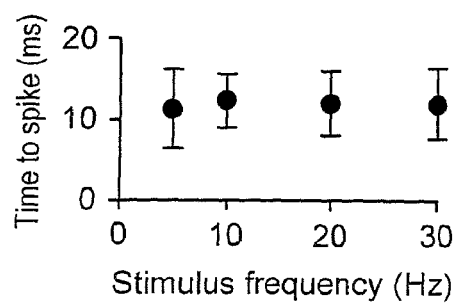
FIG. 3(e) shows the latency to spike peak throughout the light pulse train for the experiment described in FIG. 3(b).

Having established the ability of ChR2 to drive sustained naturalistic trains of spikes, we turned next to probing quantitatively the frequency response of light-spike coupling. ChR2 enabled driving of sustained spike trains from 5 to 30 Hz (FIG. 3a; here tested with series of twenty 10-ms long light pulses), as suggested by the Poisson train data (FIG. 2). For these particular cells under these particular conditions, it was easier to evoke more spikes at lower frequencies, than at higher frequencies (FIG. 3b; n=13 neurons). Light pulses delivered at 5 or 10 Hz could elicit arbitrarily long spike trains (FIG. 3b), with spike probability dropping off at higher frequencies of stimulation (20 Hz yielded 7.2+6.6 spikes, and 30 Hz yielded 4.0+6.3 spikes). For these experiments, the light pulse durations used were 5 ms (n=1), 10 ms (n=9), or 15 ms (n=3) long (data from all n=13 cells were pooled for the population analyses of FIG. 3). As expected from the observation that light pulses generally elicited single spikes (FIG. 1d and FIG. 2), almost no extraneous spikes occurred during the delivery of trains of light pulses (FIG. 3c). Even at higher frequencies, the temporal jitter of spike timing remained very low throughout the trains (<5 ms; FIG. 3d), and the latency to spike remained constant across frequencies (~10 ms throughout; FIG. 3e). Thus ChR2 can induce spiking across a physiologically relevant range of firing frequencies, appropriate for driving trains and bursts of spikes.

Example 7

Figure 4A:
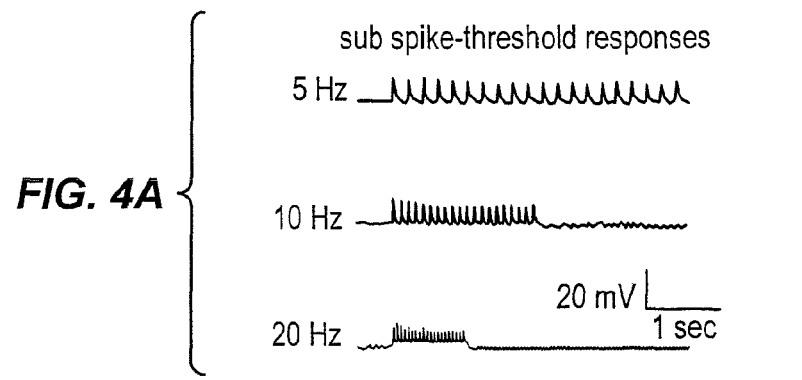
FIG. 4(a) has voltage traces showing subthreshold depolarizations in a current-clamped hippocampal neuron (left).
Figure 4B:
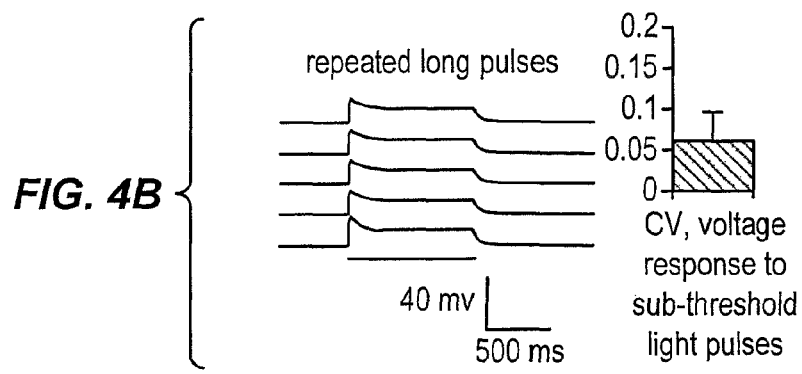
FIG. 4(b) illustrates how longer light pulses induced repeatable depolarizations. Right, coefficients of variation (CV) for the induced voltage changes (n=5 neurons).
Figure 4C:
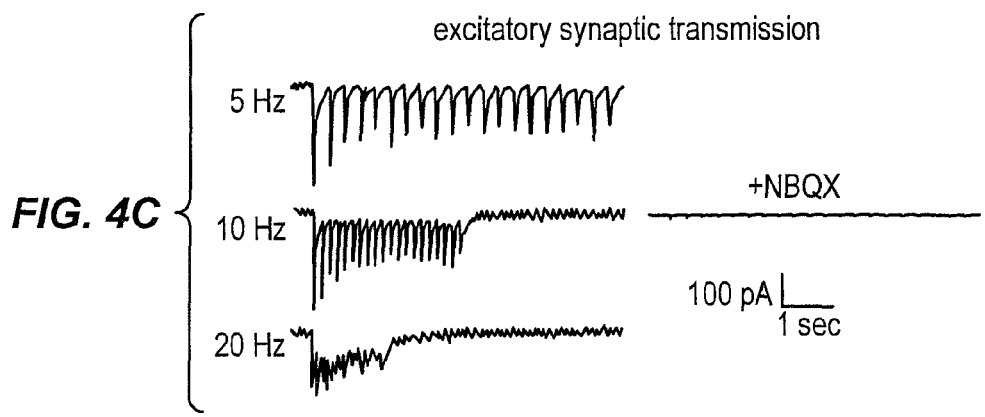
FIG. 4(c) shows excitatory synaptic transmission driven by light pulses. The glutamatergic blocker NBQX abolishes these synaptic responses (right).

It has been found that trial-to-trial variability in the subthreshold deflections evoked by repeated light pulses was quite small, with coefficient of variation 0.06+0.03 (FIG. 4b; n=5). ChR2 therefore can be employed to drive reliably timed subthreshold depolarizations with precisely determined amplitude.

Example 8

Figure 4D:
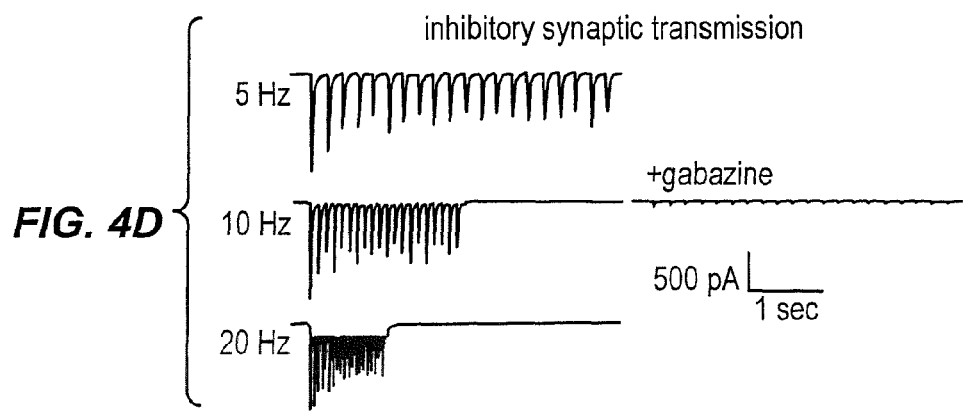
FIG. 4(d) shows inhibitory synaptic transmission driven by light pulses. The GABAergic transmission blocker gabazine abolishes these synaptic responses (right).

The high fidelity control of spiking mediated by ChR2 suggested that it would be possible to optically drive activity throughout connected neural networks, via synaptic transmission. Indeed, both excitatory (FIG. 4c) and inhibitory (FIG. 4d) synaptic events could be evoked in neurons receiving input from ChR2-expressing presynaptic neurons. These results suggest that synaptic transmission can be controlled reliably with ChR2.

Example 9

Figure 5A:
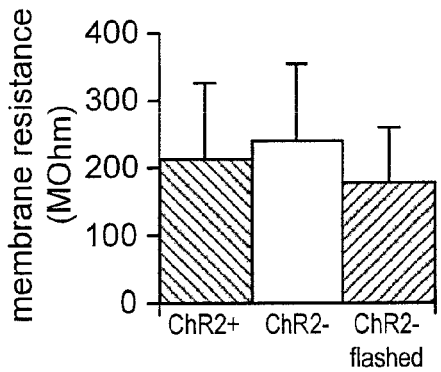
FIG. 5(a) shows membrane resistance of neurons expressing ChR2 (CHR2+; n=18), not expressing ChR2 (CHR2−; n=18), or expressing ChR2 and measured 24 hours after exposure to a light-pulse protocol (CHR2+ finished; n=12).
Figure 5B:
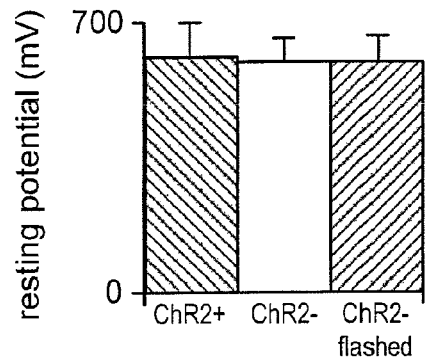
FIG. 5(b) shows membrane resting potential of the same neurons described in FIG. 5(a).
Figure 5C:
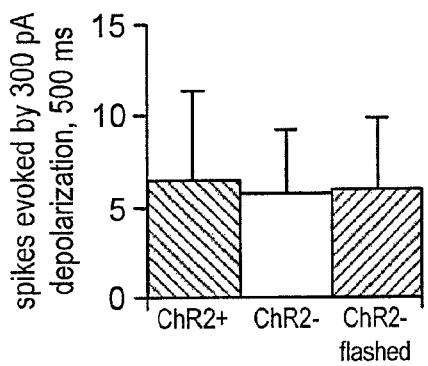
FIG. 5(c) shows the number of spikes evoked by a 300-pA depolarisation, in the same neurons.

Extensive controls were carried out to test whether expression of ChR2 in neurons perturbed their basal electrical properties, altered their dynamic electrical properties in the absence of light, or jeopardized their prospects for cellular survival. Lentiviral expression of ChR2 for at least one week did not alter neuronal membrane resistance (212+115 MΩ for ChR2+ cells vs. 239.3+113 MΩ for ChR2− cells; FIG. 5a; p>0.45; n=18 each) or resting potential (−60.6+9.0 mV for ChR2+ vs. −59.4+6.0 mV for ChR2−; FIG. 5b; p>0.60), measured in darkness. This suggests that in neurons, ChR2 has little basal electrical activity, or even passive shunting ability, in the absence of light. It also suggests that expression of ChR2 did not lead to impairment of general cell health, as indicated by electrical determination of membrane integrity. As an independent measure of membrane integrity and cell health, we stained live cultured neurons with the membrane impermeant DNA-binding dye propidium iodide (PI). ChR2+ expression did not affect the percentage of live neurons that took up PI (1/56 ChR2+ neurons vs. 1/49 ChR2− neurons; p>0.9 by $\chi^2$ test). Neither did we see any pyknotic nuclei, indicative of apoptotic degeneration, in cells expressing ChR2 (data not shown). We also checked for alterations in the dynamic electrical properties of neurons, measured in darkness. There was no difference in the voltage change resulting from 100 pA of current injected in either the hyperpolarizing (−22.6+8.9 mV for ChR2+ vs. −24.5+8.7 mV for ChR2−; p>0.50) or depolarizing (+18.9+4.4 mV for ChR2+ vs. 18.7+5.2 mV for ChR2−; p>0.90) direction, nor was there any difference in the number of spikes evoked by a half-second +300 pA current injection (6.6+4.8 for ChR2+ vs. 5.8+3.5 for ChR2−; FIG. 5c; p>0.55). Thus, in the absence of light, the presence of ChR2 does not alter cell health or ongoing electrical activity, at the level of subthreshold changes in voltage or in spike output, either by shunting current through leaky channels or by altering the voltage dependence of existing neuronal input-output relationships. These controls also suggest that there were no significant long-term plastic or homeostatic alterations in the electrical properties of neurons expressing ChR2.

Example 10

In a test of whether ChR2 predisposes neurons to light-induced problems with cellular health, we measured the electrical properties described above, after 24 hours in darkness post light-exposure to a typical pulse protocol (1 sec of 20 Hz 15-ms light flashes, once per minute, for 10 minutes). Exposure of neurons expressing ChR2 to light did not alter their basal electrical properties relative to non-flashed neurons, with cells possessing normal membrane resistance (178+81 MΩ; FIG. 5a; p>0.35; n=12) and resting potential (−59.7+7.0 mV; FIG. 5b; p>0.75). Exposure to light also did not predispose neurons to cell death, as measured by live-cell PI uptake (2/75 ChR2+ neurons vs. 3/70 ChR2− neurons; p>0.55 by $\chi^2$ test). Neurons expressing ChR2 and exposed to light flashes also had normal numbers of spikes elicited from somatic current injection (6.1+3.9; FIG. 5c; p>0.75). Thus, the membrane integrity, cell health, and basal electrical properties were normal in neurons expressing ChR2 and exposed to light.

Example 11

Retroviruses for Insertion of ChR2

Figure 6:
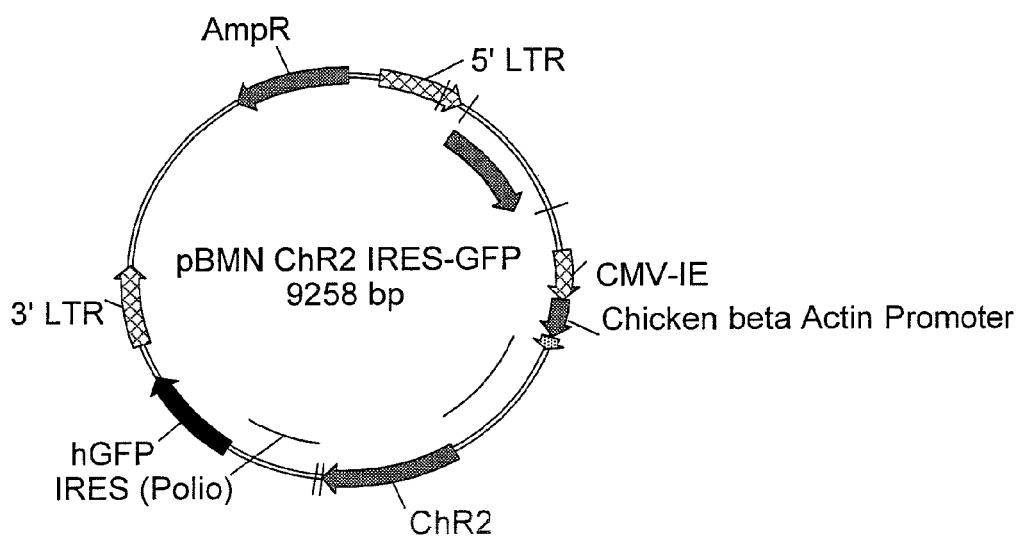
FIG. 6 shows a map of a retroviruses containing ChR2.

Moloney-type retroviruses selectively target dividing cells (Ory et al., Proc Natl Acad Sci USA 93:11400 (1996)), such as stem cells. We have constructed retroviruses containing ChR2, either fused to a fluorescent protein, or with an IRES to allow concomitant expression of a non-fusion fluorescent protein (FIG. 6). These viruses drive ChR2 under the CMV-Chicken beta actin promoter, and are VSV-G pseudotyped to permit efficacious infection of dividing mammalian cells. These retroviruses have been generated by triply transfecting the plasmid containing ChR2 with helper vectors into 293T cells. Alternatively, we have grown 293GPG cell lines in growth medium containing tetracycline, puromycin, and G418 to select for cells sustainably carrying the retroviral packaging system. Tetracycline is used to suppress the expression of VSV-G, which is toxic to 293GPG cells, during growth phase. After cells grow to 70% confluence, then tetracycline is removed to allow the expression of VSV-G. At this point, the plasmid containing Chr2 and GFP (right) are transfected into the 293GPG cells using Lipofectamine, and cultured 293GPG cells are monitored for signs of fluorescence as gene expression and retrovirus production begins. These cell lines are then frozen for future production of retrovirus. These viruses have been shown to efficaciously infect dividing cells, both in vitro (kidney cell lines, stem cells) and in vivo in rats (hippocampal stem cells, glia). This construct will be useful for targeting ChR2 to dividing cells ex vivo, for transplantation into humans for therapy, for the creation of cell lines, and for the development of animals with selective populations of labeled cells for studies of diseases of cellular activity, such as epilepsy, migraine, narcolepsy, and even autoimmune diseases.

The lentiviruses that we have generated contain tetracycline elements that allow control of the gene expression levels of ChR2, simply by altering levels of exogenous drugs such as doxycycline. This method, or other methods that place ChR2 under the control of a drug-dependent promoter, will enable control of the dosage of ChR2 in cells, allowing a given amount of light to have different effects on electrical activation, substance release, or cellular development. The lentiviruses that we have generated contain tetracycline elements that allow control of the gene expression levels of ChR2, simply by altering levels of exogenous drugs such as doxycycline.

Example 12

Stem Cell Line

Figure 7:
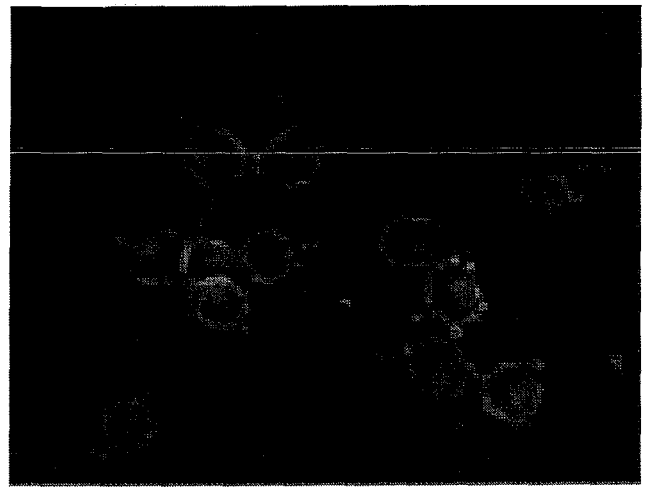
FIG. 7 shows a micrograph of a clonal stem cell line expressing ChR2 introduced by lentiviral transduction.
Figure 8:
FIG. 8 illustrates increased nuclear Ser-133 CREB phosphorylation in neural progenitor cell (NPC) triggered by light.

A clonal neural stem cell line that stably expresses ChR2-EYFP under the control of the Ef1-alpha promoter was created by infecting cultured, nondifferentiated neural stem cells with a lentivirus containing the gene for ChR2. FIG. 7 shows a micrograph of cells from this neural progenitor cell (NPC) stem cell line. This cell line is appropriate for the screening of drugs that affect the influence of electrical activity on neuronal genesis, development, or apoptosis. The stem cell line we have already made is a correct step in realizing the goal of optically controllable tissue repair, and illumination of these stem cells with light results in CREB phosphorylation, a critical step in enhancing their transformation into neurons (FIG. 8). These homogeneous stem cell lines can also be transplanted into the brain of adult animals, where they incorporate into hippocampal circuitry and can be studied functionally after 2-6 weeks.

Example 13

Transgenic Zebrafish

Figure 9:
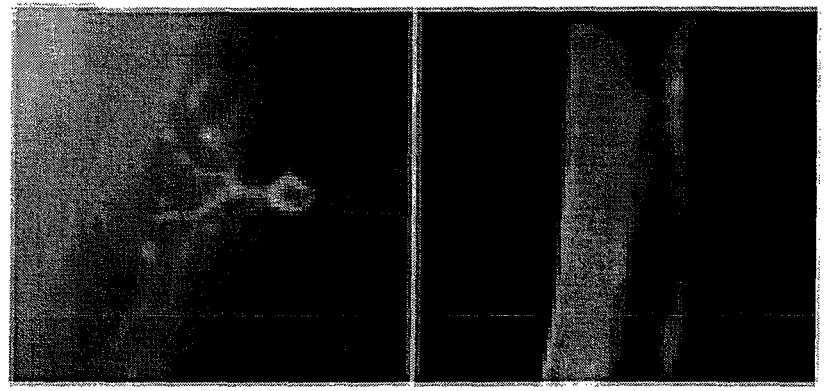
FIG. 9 is a micrograph of living zebrafish with ChR2 expressed in a neuron (left) and muscle cell (right).

Zebrafish (*Danio rerio*) embryos were acutely injected at the few-hundred cell stage with plasmid DNA containing ChR2 under promoters specific to particular cell types in the zebrafish. A random subset of cells in the zebrafish then takes up the DNA, and keeps the plasmids during fish development; specific cells will then express the ChR2 in the plasmid. FIG. 9 shows micrographs of ChR2-EYFP selectively expressed in a zebrafish trigeminal neuron (left) and in a zebrafish muscle cell (right). Briefly, larvae from 48 hours to 96 hours post fertilization were anesthetized in 0.02% tricaine in fish Ringer's solution and mounted in 1.2% agarose for imaging and photostimulation. Illumination of the live fish expressing ChR2 in muscle with blue light for 0.5 seconds caused rapid, phasic, single muscle contractions, which was never seen in zebrafish not containing ChR2. Neurons tolerated the ChR2 expression well, and were able to be loaded with fluorescent calcium dyes (e.g., Oregon Green BAPTA-1, X-rhod-1), appropriate for the monitoring of neural activity downstream of a selectively activated neuron expressing ChR2, using two-photon microscopy.

Example 14

Transgenic Fly

Flies (*Drosophila melanogaster*) have been generated that will express ChR2 under the UAS promoter, for use in the GAL4-UAS system that enables flexible control of gene expression in flies. The UAS-ChR2 flies can be crossed with a variety of GAL4 lines of *Drosophila*, taking advantage of the large number of transgenic flies that have been created over the last several years. We are crossing flies expressing UAS-ChR2 with flies containing GAL4 expressed exclusively in serotonergic and dopaminergic neurons. This will allow studies of the driving of motivated behavior and the creation of finely tuned motor patterns.

Example 15

Transgenic Worm

Worms (*C. elegans*) have been caused to express ChR2 by the injection of plasmids containing ChR2 under specific promoters into the syncytial gonad of the worm. Worms are also co-injected with a visible marker gene, to allow visual inspection of the success of generating the transgenic nematode. The gonad of the worm takes up the plasmid DNA and stores the DNA in large extrachromosomal arrays in eggs, passing the plasmid on to the worm's offspring. We have made *C. elegans* lines targeting ChR2 to the mechanosensory neuron AFD, the interneuron AIY, and also the serotonergic and dopaminergic neurons. These worms express the visible marker gene, indicating successful generation of stable lines. We are expressing ChR2 in *C. elegans* in serotonergic and dopaminergic neurons, important for the driving of motivated behavior and the creation of finely tuned motor patterns.

Example 16

Transgenic Mouse

Mice can be made to express ChR2 transgenically under the control of specific promoters (by pronuclear injection of plasmids containing ChR2 under a specific promoter), in specific loci ("knocking in" a gene into an existing locus), using BAC transgenic technology (to mimic the natural genetic environment of a gene), or by position effect variegation techniques (a transgenic method allowing genes to randomly express in tiny subsets of neurons). We are pursuing all of these avenues. To rapidly demonstrate the power of this technology, we have constructed mice that will allow ChR2 to be expressed in small subsets of neurons using position effect variegation. We have placed ChR2 underneath the promoter for the gene Thy1, an immunoglobulin superfamily member that is expressed by projection neurons in many parts of the nervous system (Gordon et al. Cell 50:445 (1987), Feng et al., Neuron 28:41 (2000)). Previous transgenics expressing GFP under control of the Thy1 promoter showed that many lines of the Thy1-GFP mice express GFP in small subsets of neurons, due to random interactions of the Thy1 promoter with local control elements (Feng et al., 2000). We have injected linearized plasmids containing Thy1-ChR2-EYFP into embryonic stem cells of mice, and these mice are currently being mated to produce offspring expressing Thy1 in specific subsets of neurons in the nervous system. These mice will prove enormously powerful for the analysis of the function of previously unknown cell types in the brain, leading to an understanding of the causal function of specific neuronal types.

Example 17

Treatment of Photoreceptor Degeneration in Rodents with ChR2

The death of photoreceptor cells caused by retinal degenerative diseases often results in a complete loss of retinal responses to light. Inner retinal neurons can be converted to photosensitive cells by delivering channelrhodopsin-2 (ChR2) using a lentivirus vector. The vectors can be constructed as described in the examples above Vector Injection Newborn (P1) rat (Sprague-Dawley and Long-Evans) and mouse (C57/BL and C3H/HeJ or rd1/rd1) pups can be anesthetized by chilling on ice. Adult mice (rd1/rd1) can be anesthetized by intraperitoneal injection of the combination of katamine (100 mg/kg) and xylakine (10 mg/kg). Under a dissecting microscope, an incision is made by scissors through the eyelid to expose the sclera. A small perforation is made in the sclera region posterior to the lens with a needle and viral vector suspension of 0.8-1.5 µl at the concentration of ~1 3×10$^{11}$ genomic particles/ml can be injected into intravitreal space through the hole with a Hamilton syringe with a 32-gauge blunt-ended needle. For each animal, usually, only one eye is injected with viral vectors carrying Chop2-GFP and the other eye is not injected or injected with viral vectors carrying GFP alone. After the injection, animals are kept on a 12/12 hr light/dark cycle. The light illumination of the room housing the animals measured at the wavelength of 500 nm is typically 6.0×10$^{14}$ photons cm$^{-2}$ s$^{-1}$.

The expression and functional properties of the ChR2 protein in the transfected retinal neurons can be measured by methods known in the art including those described herein.

Visual-Evoked Potential Recordings

Visual-evoked potential recordings are carried out in wild-type mice (C57BL/6 and 129/SV) at 4-6 months of age and in the rd1/rd1 mice at 6-11 months of age and 2-6 months after the viral vector injection. After being anesthetized by intraperitoneal injection of the combination of katamine (100 mg/kg) and acepromazine (0.8 mg/kg), animals are mounted in a stereotaxic apparatus. Body temperature is either maintained at 34° C. with a heating pat and a rectal probe or unregulated. Pupils are dilated by 1% atropine and 2.5% accu-phenylephrine. A small portion of the skull (~1.5×1.5 mm) centered about 2.5 mm from the midline and 1 mm rostral to the lambdoid suture is drilled and removed. Recordings are made from visual cortex (area V1) by a glass micropipette (resistance about 0.5 M after filled with 4 M NaCl) advanced 0.4 mm beneath the surface of the cortex at the contralateral side of the stimulated eye. The stimuli are 20 ms pluses at 0.5 Hz. Responses are amplified (1,000 to 10,000), band-pass filtered (0.3e100 Hz), digitized (1 kHz), and are averaged between 30-250 trials.

Light Stimulation

For visual evoked potential, light stimuli are generated by the monochromator and projected to the eyes through the optical fiber. The light intensity is attenuated by neutral density filters. The light energy is measured by a thin-type sensor (TQ82017) and an optical power meter (Model: TQ8210) (Advantest, Tokyo, Japan).

Example 18

Treatment of Hyperglycemia in Mice by Transplantation of Macronencapsulated ChR2 Transfected Islets Macroencapsulated islets can reverse hyperglycemia in diabetic animals when transplanted i.p., s.c., or into the fat pad. Transplantation of macroencapsulated ChR2 transfected islets would provide a method for control the release of insulin in a temporally precise manner. This can be accomplished by transfecting islets with ChR2 and implanting these cells into the skin of the animal and then driving their activation using light.

Animals

Male Swiss Webster nude mice (Taconic, Germantown, N.Y.) of 25-30 g can be made diabetic with 250 mg/kg body weight (bw) i.p. injection of 4% streptozocin (STZ*) (Sigma, St. Louis, Mo.) dissolved in citrate buffer, pH 4.5. Only animals with blood glucose concentrations above 350 mg/dl are then used as recipients. Sprague Dawley (SD) rats (Taconic) of about 250 g are used as donors. All animals would be kept under conventional conditions in acclimatized rooms with free access to standard pelleted food and tap water. Nonfasting blood glucose levels and body weight (bw) of recipients are measured on the day of transplantation and then weekly for the next 7 weeks. Blood glucose concentrations can be measured with a One Touch II portable glucometer (Lifescan Inc., Milpitas, Calif.). Additional samples of plasma from freely fed and fasted normal mice and rats are collected to compare the relationship between plasma glucose and whole blood glucose in donor and recipient strains. Plasma glucose values can be assessed by a Glucose Analyzer 2 (Beckman, Palo Alto, Calif.).

Islet Isolation

Rat islets are isolated technique known in the art. For example, 1-2 mg/ml collagenase P (Boehringer Mannheim, Indianapolis, Ind.) solution is injected into the pancreatic duct and the pancreas is digested for 19 min at 37° C.; islets are then separated from the exocrine tissue using discontinuous Histopaque-1077 (Sigma) density gradient centrifugation. Islets with diameters of 50-250 µm are hand picked, counted, and cultured in RPMI-1640 tissue culture medium with the standard glucose concentration of 200 mg/dl, supplemented with 10% fetal calf serum, 100 U/ml penicillin, and 100 mg/ml streptomycin.

Islet can be transfected with ChR2 as described in the previous examples. Expression and functional properties of ChR2 protein in the transfected cells can be measured by methods known in the art including those described herein.

Macroencapsulation and Transplantation

Ported devices (Thera Cyte™) with an internal volume of 20 µl, can be used for islet macroencapsulation. The devices are fabricated from membrane laminates composed of three layers: a cell-retentive membrane with a nominal pore diameter of 0.45 µm laminated to an outer 5 µm pore diameter polytetrafluoroethylene vascularizing membrane with an outer polyester mesh providing support. The membrane laminates in a rectangular shape is sealed on edges by ultrasonic welding. At one end of the device, polyethylene tubing is attached to provide access to the lumen. Aliquots of 1200 islets are suspended in a volume of 20 µl in Eppendorf tubes and transferred through the port into the lumen of the device with a Hamilton syringe; the tubing is sealed with Silastic silicon glue (Dow Corning Corp., Midland, Mich.). Transplantation can be performed under Metofane anesthesia. When implanted s.c., a skin incision of about 2 cm is made on the back right side of the animal, followed by preparation of a s.c. pocket with gentle blunt dissection. The device is inserted into the pocket, and the incision was closed with wound clips.

The cells can be activated to release insulin with a light-emitting diode or a laser with an optical fiber attached to the end or by the methods described herein.

Glucose Tolerance Tests

Seven weeks after transplantation, IPGTTs are performed (glucose 2 g/kg bw, injected as a 10% solution). Before the glucose challenge, all animals fast for about 16 hr. Samples from snipped tails for the blood glucose are taken at 0, 15, 30, 60, 90 and 120 min after glucose injection.

Example 19

Generation of Dopaminergic ChR2 Transfected Neurons in Hollow Fibers

Effect of PA6 CM on ES Cell Differentiation

ES cells are cultured using PA6 CM to induce neural differentiation. To prepare PA6 conditioned medium (CM), confluent PA6 cells are washed three times with phosphate-buffered saline with calcium and magnesium ions [PBS(+)] and then the respective media are replaced by G-MEM supplemented with 5% KSR, 0.1 mM non-essential amino acids, 1 mM pyruvate and 0.1 mM 2-mercaptoethanol without/with heparin (10 or 100 mg/ml). After 48 h, the supernatant is collected and filtered with a 0.22 mm filter. CM collected using GMEM based media without, with 10 mg/ml and with 100 mg/ml heparin are referred to as CM-0H, CM-10H and CM-100H, respectively.

ES cells are plated on polyornithine (Sigma)/fibronectin (Invitrogen)-coated glass plates at a density of 1250 cells/cm_2 in G-MEM supplemented with 5% KSR, 0.1 mM non-essential amino acids, 1 mM pyruvate and 0.1 mM 2-mercaptoethanol. After 5 h, CM-0H, CM-10H (final concentration of heparin is 3.3 mg/ml) or CM-100H (final concentration of heparin is 33 mg/ml) is added to the culture plate to 13 volume of the culture medium and mixed well. All culture dishes are maintained at 37° C. in air containing 5% $CO_2$ for 16 days.

Differentiation of ES Cells in Hollow Fibers

Hollow fibers, fabricated from semi-permeable polymer membranes and available in a variety of diameters and wall thickness, are bundled into a housing and are used extensively in extracorporeal artificial organs, such as artificial kidney and artificial lung. Three different kinds of hollow fibers can be used here. FB-150F fibers are used for Haemodialysis (NIPRO, Osaka, Japan) and are made of cellulose triacetate with a 200 mm internal diameter and 15 mm thickness wall. Evafluxs 2A and Evafluxs 5A fibers are used for plasmapheresis (Kuraray, Okayama, Japan) and are made of ethylene vinyl alcohol copolymer with a 175 mm internaldiameter and 40 mm thickness wall. Hollow fibers of FB-150F, Evafluxs 2A or Evafluxs 5A are referred to as HF-1, HF-2 or HF-3, and their molecular weight cutoff values are 55 kDa (95% cutoff), 144 kDa (90% cutoff) and 570 kDa (90% cutoff), respectively. ES cells are dissociated into single cells by treating them with 0.25% trypsin and 1 mM EDTA in PBS. The cells are loaded into a 1 ml syringe at a concentration of $1 \times 10^7$ cells/ml and are gently injected into hollow fibers 9 cm in length. ES cell-loaded fibers are placed in 100 mm cell culture dishes and are maintained in G-MEM supplemented with 5% KSR, 0.1 mM non-essential amino acids, 1 mM pyruvate, 0.1 mM 2-mercaptoethanol and 33% CM-10H. All culture dishes are kept in air containing 5% $CO_2$ at 37 1C for 16 days.

ES cells can be transfected with ChR2 prior or after differentiation by the methods described herein.

Cell growth of culture cells can be performed by methods known in the art. Differentiation of ES cells into dopaminergic neurons can be performed by methods known in the art such as immunofluorescence analysis and RT-PCR. Dopamine levels can be determined by methods knows in the art such as Reverse-phase HPLC.

The expression and functional properties of the ChR2 protein in the transfected cells can be measured by methods known in the art including those described herein.

Generation of dopaminergic ChR2 transfected neurons in hollow fibers is a promising approach to perform cell therapy, for example, of Parkinson's disease. This method allows for the collection and encapsulation of dopaminergic ES progeny with minimal damage and protection of implanted cells from the host immune system, which are two of the obstacles encounter today. Furthermore, ChR2 protein expression in the dopaminergic neurons allows for the control release of dopamine into the brain according to the methods described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby. Eliciting synaptic transmission demonstrates that ChR2 is an ideal tool for the temporally precise analysis of neural circuits.

What is claimed is:

1. An implantable prosthetic device comprising a cell expressing a channelrhodopsin, wherein the channelrhodopsin comprises an amino acid sequence having at least about 95% amino acid sequence identity to the amino acid sequence set forth in SEQ ID NO:1, and wherein the cell is a retinal cell, a spiral ganglion cell, or a neuron.

2. The implantable device of claim 1, wherein the channelrhodopsin comprises an amino acid sequence having at least about 98% amino acid sequence identity to the amino acid sequence set forth in SEQ ID NO:1.

3. The implantable device of claim 1, wherein the retinal cell is an amacrine cell or a bipolar cell.

4. The implantable device of claim 1, wherein the cell is a spiral ganglion cell.

5. The implantable device of claim 4, further comprising:
a) a microphone to detect sound;
b) a microprocessor to analyze the frequency components of the sound and convert them to light-emitting diode (LED) signals; and
c) a plurality of LEDs that emit light in a spatially patterned fashion.

6. The implantable device of claim 1, wherein the cell is a neuron.

7. The implantable device of claim 1, further comprising an implantable light source.

8. The implantable device of claim 1, wherein the channelrhodopsin is encoded by a nucleotide sequence present in a viral vector, wherein the channelrhodopsin-encoding nucleotide sequence is operably linked to a cell-specific promoter.

9. The implantable device of claim 8, wherein the cell-specific promoter is a somatostatin promoter, a parvalbumin promoter, a GABA-6 promoter, a calbindin promoter, or an EF1-alpha promoter.

10. The implantable device of claim 8, wherein the viral vector is a lentivirus vector or a retroviral vector.

11. A system comprising:
a) an implantable prosthetic device comprising a cell expressing a channelrhodopsin, wherein the channelrhodopsin comprises an amino acid sequence having at least about 95% amino acid sequence identity to the amino acid sequence set forth in SEQ ID NO:1, and wherein the cell is a retinal cell, a spiral ganglion cell, or a neuron; and
b) an implantable light source.

12. The system of claim 11, wherein
wherein the channelrhodopsin comprises an amino acid sequence having at least about 98% amino acid sequence identity to the amino acid sequence set forth in SEQ ID NO:1.

13. The system of claim 11, wherein the retinal cell is an amacrine cell or a bipolar cell.

14. The system of claim 11, wherein the cell is a spiral ganglion cell.

15. The system of claim 14, further comprising:
a) a microphone to detect sound;
b) a microprocessor to analyze the frequency components of the sound and convert them to light-emitting diode (LED) signals; and
c) a plurality of LEDs that emit light in a spatially patterned fashion.

16. The system of claim 11, wherein the cell is a neuron.

17. The system of claim 16, wherein the neuron is a dopaminergic neuron.

18. The system of claim 11, wherein the channelrhodopsin is encoded by a nucleotide sequence present in a viral vector, wherein the channelrhodopsin-encoding nucleotide sequence is operably linked to a cell-specific promoter.

19. The system of claim 18, wherein the cell-specific promoter is a somatostatin promoter, a parvalbumin promoter, a GABAα6 promoter, a calbindin promoter, or an EF1-alpha promoter.

20. The system of claim 18, wherein the viral vector is a lentivirus vector or a retroviral vector.

21. An implantable prosthetic device comprising:
a) a cell expressing a channelrhodopsin, wherein the channelrhodopsin comprises an amino acid sequence having at least about 95% amino acid sequence identity to the amino acid sequence set forth in SEQ ID NO:1, and wherein the cell is a spiral ganglion cell; and
b) a light source.

22. The implantable device of claim 21, wherein the channelrhodopsin comprises an amino acid sequence having at least about 98% amino acid sequence identity to the amino acid sequence set forth in SEQ ID NO:1.

23. The implantable device of claim 21, wherein the light source is a light-emitting diode (LED).

24. The implantable device of claim 23, further comprising:
a) a microphone to detect sound;
b) a microprocessor to analyze the frequency components of the sound and convert them to light-emitting diode (LED) signals; and
c) a plurality of LEDs that emit light in a spatially patterned fashion.

* * * * *

SEQUENCE LISTING

```
<160> NUMBER OF SEQ ID NOS: 5

<210> SEQ ID NO 1
<211> LENGTH: 310
<212> TYPE: PRT
<213> ORGANISM: Chlamydomonas reinhardtii

<400> SEQUENCE: 1

Met Asp Tyr Gly Gly Ala Leu Ser Ala Val Gly Arg Glu Leu Leu Phe
  1               5                  10                  15

Val Thr Asn Pro Val Val Val Asn Gly Ser Val Leu Val Pro Glu Asp
             20                  25                  30

Gln Cys Tyr Cys Ala Gly Trp Ile Glu Ser Arg Gly Thr Asn Gly Ala
         35                  40                  45

Gln Thr Ala Ser Asn Val Leu Gln Trp Leu Ala Ala Gly Phe Ser Ile
     50                  55                  60
```

```
Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro
305                 310

<210> SEQ ID NO 2
<211> LENGTH: 930
<212> TYPE: DNA
<213> ORGANISM: Chlamydomonas reinhardtii

<400> SEQUENCE: 2
atggattatg gaggcgccct gagtgccgtt gggcgcgagc tgctatttgt aacgaaccca      60
gtagtcgtca atggctctgt acttgtgcct gaggaccagt gttactgcgc gggctggatt     120
gagtcgcgtg gcacaaacgg tgcccaaacg cgtcgaacg tgctgcaatg gcttgctgct      180
ggcttctcca tcctactgct tatgttttac gcctaccaaa catggaagtc aacctgcggc     240
tgggaggaga tctatgtgtg cgctatcgag atggtcaagg tgattctcga gttcttcttc     300
gagtttaaga acccgtccat gctgtatcta gccacaggcc accgcgtcca gtggttgcgt     360
tacgccgagt ggcttctcac ctgcccggtc attctcattc acctgtcaaa cctgacgggc     420
ttgtccaacg actacagcag gcgcaccatg ggtctgcttg tgtctgatat tggcacaatt     480
gtgtggggcg ccacttccgc catggccacc ggatacgtca aggtcatctt cttctgcctg     540
ggtctgtgtt atggtgctaa cacgttcttt cacgctgcca aggcctacat cgagggttac     600
cacaccgtgc cgaagggccg tgtcgccag tggtgactg gcatggcttg gctcttcttc       660
```

```
gtatcatggg gtatgttccc catcctgttc atcctcggcc ccgagggctt cggcgtcctg    720
agcgtgtacg gctccaccgt cggccacacc atcattgacc tgatgtcgaa gaactgctgg    780
ggtctgctcg gccactacct gcgcgtgctg atccacgagc atatcctcat ccacggcgac    840
attcgcaaga ccaccaaatt gaacattggt ggcactgaga ttgaggtcga dacgctggtg    900
gaggacgagg ccgaggctgg cgcggtaccc                                     930
```

<210> SEQ ID NO 3
<211> LENGTH: 930
<212> TYPE: DNA
<213> ORGANISM: Chlamydomonas reinhardtii

<400> SEQUENCE: 3

```
atggactatg gcggcgcttt gtctgccgtc ggacgcgaac ttttgttcgt tactaatcct     60
gtggtggtga acgggtccgt cctggtccct gaggatcaat gttactgtgc cggatggatt    120
gaatctcgcg gcacgaacgg cgctcagacc gcgtcaaatg tcctgcagtg gcttgcagca    180
ggattcagca ttttgctgct gatgttctat gcctaccaaa cctggaaatc tacatgcggc    240
tgggaggaga tctatgtgtg cgccattgaa atggttaagg tgattctcga gttcttttt     300 gagtttaaga atccctctat gctctacctt gccacaggac accgggtgca gtggctgcgc    360
tatgcagagt ggctgctcac ttgtcctgtc atccttatcc acctgagcaa cctcaccggc    420
ctgagcaacg actacagcag gagaaccatg ggactccttg tctcagacat cgggactatc    480 gtgtggggg ctaccagcgc catggcaacc ggctatgtta agtcatctct cttttgtctt     540
ggattgtgct atggcgcgaa acattttttt cacgccgcca agcatatat cgagggttat     600 catactgtgc caaagggtcg gtgccgccag gtcgtgaccg gcatggcatg gctgttttc     660 gtgagctggg gtatgttccc aattctcttc attttggggc ccgaaggttt tggcgtcctg    720
agcgtctatg gctccaccgt aggtcacacg attattgatc tgatgagtaa aaattgttgg    780
gggttgttgg gacactacct gcgcgtcctg atccacgagc acatattgat tcacggagat    840
atccgcaaaa ccaccaaact gaacatcggc ggaacggaga tcgaggtcga gactctcgtc    900
gaagacgaag ccgaggccgg agccgtgcca                                     930
```

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 4

```
ggcagcgctg ccaccatgga ttatggaggc gccctgagt                            39
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 5

```
ggcactagtc tattacttgt acagctcgtc                                      30
```